(12) United States Patent
Lemaire et al.

(10) Patent No.: US 6,646,106 B1
(45) Date of Patent: Nov. 11, 2003

(54) OPTICALLY ACTIVE LINEAR POLYMER USED AS LIGAND IN THE PREPARATION OF METALLIC COMPLEXES DESIGNED FOR ASYMMETRIC CATALYSIS

(75) Inventors: Marc Lemaire, Villeurbanne (FR); Rob Ter Halle, Collonges Au Mont d'Or (FR); Emmanuelle Schulz, Sainte-Foy-les-Lyon (FR); Benoît Colasson, Sainte-Luce-sur-Loire (FR); Michel Spagnol, Meyzieu (FR); Christine Saluzzo, Lyons (FR); Thierry Lamouille, Lyons (FR)

(73) Assignees: Rhodia Chimie, Boulogne Billancourt Cedex (FR); Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 09/914,613

(22) PCT Filed: Jan. 14, 2000

(86) PCT No.: PCT/FR00/00082

§ 371 (c)(1),
(2), (4) Date: Dec. 11, 2001

(87) PCT Pub. No.: WO00/52081

PCT Pub. Date: Sep. 8, 2000

(30) Foreign Application Priority Data

Mar. 1, 1999 (FR) .............................. 99 02510

(51) Int. Cl.$^7$ ................................................. C08G 79/02
(52) U.S. Cl. ............................ 528/398; 528/51; 528/52; 528/56; 528/485; 528/492
(58) Field of Search .............................. 528/398, 51, 52, 528/56, 485, 492

(56) References Cited

U.S. PATENT DOCUMENTS 5,631,345 A * 5/1997 Takaya et al.

FOREIGN PATENT DOCUMENTS

| EP | 0 728 768 A2 | 8/1996 |
| WO | WO 97/02232 A1 | 1/1997 |
| WO | WO 98/12202 A1 | 3/1998 |

\* cited by examiner

*Primary Examiner*—Duc Truong
(74) *Attorney, Agent, or Firm*—Burns, Doane, Swecker & Mathis, L.L.P.

(57) ABSTRACT

The invention concerns optically active polymers, obtainable by polymerizing chiral diphosphine having a C2 axis of symmetry, excluding all other symmetry element, with one or several polymerizable monomers, said chiral diphosphine consisting of a chiral body bearing two identical functional groups capable of reacting with said polymerizable monomers.

36 Claims, No Drawings

OPTICALLY ACTIVE LINEAR POLYMER USED AS LIGAND IN THE PREPARATION OF METALLIC COMPLEXES DESIGNED FOR ASYMMETRIC CATALYSIS

The invention relates to an optically active diphosphorated polymeric ligand of use in the preparation of metal complexes intended for asymmetric catalysis.

Asymmetric catalysis has experienced considerable growth in recent years. It exhibits the advantage of resulting directly in the preparation of optically pure isomers by asymmetric induction, without it being necessary to carry out resolution of racemic mixtures.

2,2'-Bis(diphenylphosphino)-1,1'-binaphthyl (BINAP) is an example of a diphosphorated ligand commonly used in the preparation of metal complexes for the asymmetric catalysis of hydrogenation, carbonylation or hydrosilylation reactions, reactions for the formation of C—C bonds (such as allylic substitutions or Grignard cross-couplings) or even reactions for the asymmetric isomerization of allylamines.

The metal complexes prepared from BINAP are complexes of rhodium, iridium, palladium, platinum or ruthenium, which are very expensive metals.

Because of the high cost of the metals constituting them, industrial processes using these metal complexes as catalyst necessarily comprise stages devoted to their recovery and to their recycling.

In point of fact, metal complexes of the type of those prepared from BINAP are generally employed in homogeneous catalysis, that is to say that they are used in solution in the reaction medium.

Under these circumstances, the stages of extraction of the catalyst and of recovery are complex and render the implementation of these processes on an industrial scale problematic and laborious.

The invention is targeted at solving this problem by providing in particular a more economical process in which the stages of extraction of the catalyst, of recovery and of recycling are simplified and are compatible with implementation of the process on an industrial scale. According to this process, the metal catalyst is solid and is separated from the reaction medium by simple filtration, the catalysis taking place in the heterogeneous phase.

The novelty of the invention is based on the specific nature of the metal complex used as catalyst and more specifically on the nature of the phosphorated ligand used to prepare the catalyzing metal complex, which nature determines the feature of low solubility of the catalyst.

The development of phosphorated metal complexes which can be used in heterogeneous catalysis and which can be separated from the reaction medium by filtration has already been envisaged in the art.

D. J. Bayston et al. have described, in J. Org. Chem., 1998, 63, 3137–3140, a catalyst prepared from a polymer ligand composed of a chiral diphosphine grafted to a polymer support. The formula of this ligand can be represented diagrammatically as follows, where PS denotes a polymer support composed of polystyrene and Ph denotes the phenyl radical:

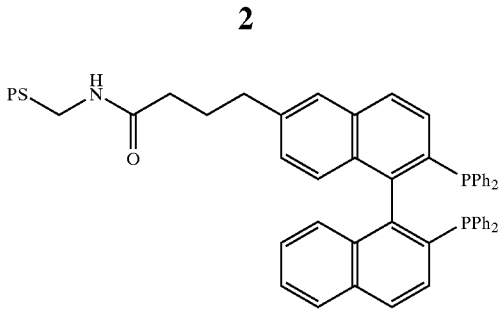

More generally WO 98/12202 discloses polymer ligands for the preparation of metal complexes intended for asymmetric catalysis. These ligands, of formula:

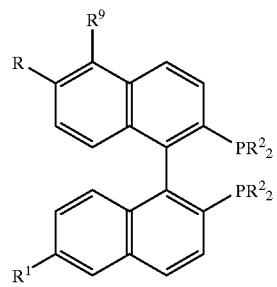

in which $R^1$ is —$Y^0$—$X^0$—$R^4$ where $R^4$ comprises an insoluble support derived from a polystyrene, from a polyamide or from a polymer resin, are also composed of a chiral diphosphine grafted to a polymer support.

The catalyzing complexes prepared from the ligands of the prior art only exhibit a single chiral site per polymer chain, which requires the involvement of large catalytic masses for effective catalysis, the mass of the polymer chain adding to the mass of the grafted chiral molecule.

Furthermore, the ligands of the prior art do not exhibit the $C_2$ axial symmetry of the BINAP molecule. In point of fact, it is known that polymeric ligands with $C_2$ axial symmetry result in excellent enantiomeric selectivities in the catalysis of asymmetric reactions.

The polymer of the invention which can be used as ligand in the preparation of catalyst complexes exhibits several optically active centers and a variable structure, which allows in particular the preparation of polymers exhibiting, as a whole, $C_2$ axial symmetry.

The polymer of the invention is composed of a linkage of two types of units.

The first type of unit is the residue of a chiral diphosphine exhibit a $C_2$ axis of symmetry, with the exclusion of any other element of symmetry, and carrying two identical polymerizable functional groups.

The second type of unit is the residue of a monomer which can polymerize with said functional groups, that is to say a monomer comprising two identical functional groups capable of reacting with the functional groups of the chiral diphosphine.

Due to the recurrence of the chiral unit in the polymer chain, much lower amounts of the corresponding metal catalyst are necessary for effective catalysis of the asymmetric reactions. Furthermore, starting from a polymerizable monomer also exhibiting a $C_2$ axis of symmetry, a polymer is obtained exhibiting, as a whole, $C_2$ axial symmetry, which leads to much better enantio-selectivity in comparison with the grafted polymers of the prior art.

More specifically, the invention relates to an optically active polymer which can be used as ligand in the preparation of metal complexes intended for asymmetric catalysis. These polymers can be obtained by polymerization of a chiral diphosphine exhibiting a $C_2$ axis of symmetry, with the exclusion of any other element of symmetry, with one or more polymerizable monomers. According to the invention, the chiral diphosphine is composed of a chiral body (or chiral backbone) carrying two identical functional groups capable of reacting with the polymerizable monomers.

The notion of $C_2$ axis of symmetry and plane of symmetry is described by Kurt Mislow in "Introduction to stereochemistry", W. A. Benjamin Inc. New York, Amsterdam, 1965.

A molecule exhibiting a $C_2$ axis of symmetry is such that, by rotation of this molecule by 180° about the axis of symmetry, a molecule is obtained which is exactly superimposable on it.

The chiral diphosphines which can be used in the preparation of the polymers of the invention include molecules with a chirality which results from the spatial arrangement of the atoms constituting them (these molecules are described as atropisomers), molecules with a chirality carried by the phosphorus atoms and molecules with a chirality carried by carbon atoms.

The diphosphines of atropisomer type do not comprise an asymmetric carbon. In these molecules, rotation about single bonds is prevented or greatly slowed down.

Atropisomeric diphosphines which are particularly preferred are those having a chiral body (or backbone) corresponding to the following formula:

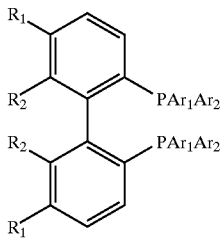

I.1 in which:

Ar$_1$ and Ar$_2$ are independently a saturated, unsaturated or aromatic carbocycle;

R$_1$ and R$_2$ are independently a hydrogen atom; a Z group; or an —XZ group where X is O, S or —NT; and Z and T are selected independently from a saturated aliphatic hydrocarbonaceous group optionally interrupted by O, S and/or N; a saturated, unsaturated or aromatic carbocyclic group; or a saturated aliphatic hydrocarbonaceous group substituted by one or more saturated, unsaturated or aromatic carbocyclic groups, in which the aliphatic group is optionally interrupted by O, S and/or N; it being understood that T can additionally be a hydrogen atom; or else two R$_1$ and R$_2$ groups, attached to the same phenyl nucleus, together form an unsaturated or aromatic carbocycle or alternatively together form an unsaturated or aromatic heterocycle.

In the context of the invention, the term "carbocyclic radical" is understood to mean an optionally substituted monocyclic or polycyclic, preferably $C_3$–$C_{50}$, radical. It is advantageously a $C_3$–$C_{18}$ radical, preferably a mono-, bi- or tricyclic radical.

When the carbocyclic radical comprises more than one ring (case of polycyclic carbocycles), the rings can be condensed two by two or attached two by two via σ bonds. Two condensed nuclei can be orthocondensed or pericondensed.

The carbocyclic radical can comprise a saturated part and/or an aromatic part and/or an unsaturated part.

Cycloalkyl groups are examples of saturated carbocyclic radicals.

The cycloalkyl groups are preferably $C_3$–$C_{18}$ groups and better still $C_3$–$C_{10}$ groups. Mention may in particular be made of the cyclopentyl, cyclohexyl, cycloheptyl, cyclooctyl, adamantyl or norbornyl radicals.

The unsaturated carbocycle or any unsaturated part exhibits one or more ethylenic unsaturations. It preferably exhibits from 6 to 50 carbon atoms, better still from 6 to 20, for example from 6 to 18.

$C_6$–$C_{10}$ cycloalkenyl groups are examples of unsaturated carbocycles.

($C_6$–$C_{18}$)aryl groups and in particular phenyl, naphthyl, anthryl and phenanthryl groups are examples of aromatic carbocycle radicals.

The term "aliphatic hydrocarbonaceous group" is understood to mean a saturated, linear or branched, optionally substituted group preferably comprising from 1 to 25 carbon atoms.

Advantageously, said aliphatic hydrocarbonaceous group is alkyl comprising 1 to 12 carbon atoms, better still comprising 1 to 6 carbon atoms.

The methyl, ethyl, propyl, isopropyl, butyl, isobutyl, t-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 2-ethylbutyl, 1-methyl-1-ethylpropyl, heptyl, 1-methylhexyl, 1-propylbutyl, 4,4-dimethylpentyl, octyl, 1-methylheptyl, 2-ethylhexyl, 5,5-dimethylhexyl, nonyl, decyl, 1-methylnonyl, 3,7-dimethyloctyl and 7,7-dimethyloctyl radicals are examples of alkyl groups.

The substituents of the carbocyclic radicals (St1) can be saturated aliphatic hydrocarbonaceous groups optionally interrupted by O, S and/or N, or —XZ groups in which X and Z are as defined above.

The substituents of the aliphatic hydrocarbonaceous radicals (St2) are saturated or unsaturated carbocyclic groups, themselves optionally substituted by one or more of the substituents (St1) defined above.

Preferably, Ar$_1$ and Ar$_2$ are independently ($C_3$–$C_8$)cycloalkyl or ($C_6$–$C_{18}$)aryl, optionally substituted by one or more ($C_1$–$C_6$)alkyl and/or ($C_1$–$C_6$)alkoxy; and R$_1$ and R$_2$ are independently a hydrogen atom; ($C_3$–$C_8$)cycloalkyl; ($C_1$–$C_6$)alkyl; ($C_1$–$C_6$)alkoxy or ($C_6$–$C_{18}$)aryl, the cycloalkyl and aryl groups optionally being substituted by ($C_1$–$C_6$)alkyl and/or ($C_1$–$C_6$)alkoxy.

When R$_1$ and R$_2$ together form an unsaturated carbocycle or heterocycle, the latter preferably exhibits a single unsaturation, which is that shared with the phenyl nucleus carrying the R$_1$ and R$_2$ groups.

The aromatic carbocycles which R$_1$ and R$_2$ together form are preferably as defined above.

The unsaturated carbocycles which R$_1$ and R$_2$ together form are mono- or polycyclic, the definition of these terms being as put forward above. These carbocycles preferably comprise from 6 to 50 carbon atoms, better still from 6 to 20 carbon atoms. $C_6$–$C_{10}$ cycloalkenyl are in particular examples thereof.

The term "heterocycle" is understood to mean, according to the invention, mono- or polycyclic and in particular mono-, bi- or tricyclic radicals comprising one or more heteroatoms chosen from O, S and/or N, preferably 1 to 4 heteroatoms.

When the heterocycle is polycyclic, the latter can be composed of several monocycles condensed two by two (orthocondensed or pericondensed) and/or several monocycles attached two by two via 94 bonds.

Preferably, the monocycles or monocycle constituting the heterocycle has from 5 to 12 ring members, better still from 5 to 10 ring members, for example from 5 to 6 ring members.

When $R_1$ and $R_2$ form a heterocycle, the latter comprises an unsaturated part and/or an aromatic part, it being understood that the unsaturated part preferably comprises a single double bond.

Pyridine, furan, thiophene, pyrrole, pyrazole, imidazole, thiazole, isoxazole, isothiazole, pyridazine, pyrimidine, pyrazine, triazines, indolizine, indole, isoindole, benzofuran, benzothiophene, indazole, benzimidazole, benzothiazole, purine, quinoline, isoquinoline, cinnoline, phthalazine, quinazoline, quinoxaline, pteridine, naphthyridines, carbazole, phenothiazine, phenoxazine, acridine, phenazine, oxazole, pyrazole, oxadiazole, triazole, thiadiazole and their unsaturated derivatives are examples of unsaturated or aromatic mono- or polycyclic heterocycles. The unsaturated derivatives of pyrrolidine, dioxolane, imidazolidine, pyrazolidine, piperidine, dioxane, morpholine, dithiane, thiomorpholine, piperazine and trithiane are other examples.

Pyridine, furan, thiophene, pyrrole, benzofuran and benzothiophene in particular are particularly preferred heterocycles.

Preference is given, in the context of the invention, to monocyclic or bicyclic carbocycles and heterocycles.

According to the invention, when $R_1$ and $R_2$ together form carbocycle or heterocycle, the latter can optionally be substituted by one or more substituents St1 as defined above.

Advantageously:

$Ar_1$ and $Ar_2$ are independently a saturated, unsaturated or aromatic monocyclic carbocycle optionally substituted by one or more $(C_1-C_6)$alkyl or $(C_1-C_6)$alkoxy groups exhibiting from 3 to 8 carbon atoms;

$R_1$ and $R_2$ are independently selected from a hydrogen atom, a $(C_1-C_6)$alkyl group or a $(C_1-C_6)$alkoxy group; or else $R_1$ and $R_2$ form, together with the carbon atoms which carry them, (i) an unsaturated or aromatic and monocyclic or polycyclic carbocycle exhibiting from 5 to 13 atoms or (ii) an unsaturated or aromatic and monocyclic or polycyclic heterocycle exhibit from 4 to 12 carbon atoms and one or more heteroatoms selected from O, S and N, said heterocycle and said carbocycle optionally being substituted by one or more $(C_1-C_6)$alkyl or $(C_1-C_6)$alkoxy.

In this subgroup of compounds, alkyl is preferably a linear or branched, saturated $C_1-C_6$ hydrocarbonaceous radical, such as methyl, ethyl, propyl, isopropyl, butyl, isobutyl, t-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 2-ethylbutyl or 1-methyl-1-ethylpropyl.

The alkyl radical preferably comprises 1 to 4 carbon atoms.

The term "alkoxy" denotes the —O-alkyl radical, where alkyl is as defined above.

When the carbocycle is unsaturated, it more particularly comprises 1 to 2 ethylenic double bonds.

$C_3-C_{11}$ cycloalkyls, $C_6-C_{10}$ aryls and their more or less saturated derivatives are preferred examples of carbocycles.

Cyclobutyl, cyclopentyl, cyclohexyl, cycloheptyl and cyclooctyl are preferred as cycloalkyl, cyclopentane and cyclohexane being the most advantageous.

Mention may be made, as preferred $C_6-C_{10}$ aryl derivative, of the phenyl and napthyl nuclei.

In the above formula I.1, the $R_1$, $R_2$, $Ar_1$ and $Ar_2$ substituents are such that the chiral body and thus the diphosphine has a $C_2$ axis of symmetry.

Thus, when $Ar_1$, $Ar_2$, $R_1$ and/or $R_2$ represents a substituted carbocycle or heterocycle, the position and the nature of the substituents is chosen so as to retain $C_2$ axial symmetry of the molecule as a whole.

Optionally substituted $(C_3-C_8)$cycloalkyl or optionally substituted $(C_5-C_6)$aryl are preferred meanings of the $Ar_1$ and $Ar_2$ substituents. Better still, $Ar_1$ and $Ar_2$ are selected from phenyl optionally substituted by one or more $(C_1-C_6)$alkyl or $(C_1-C_6)$alkoxy; or $(C_4-C_8)$cycloalkyl optionally substituted by one or more $(C_1-C_6)$alkyl groups.

According to a particularly preferred embodiment, $Ar_1$ and $Ar_2$ are independently cyclohexyl, phenyl or tolyl.

Those compounds of formula I.1 for which $Ar_1$ and $Ar_2$ are identical are particularly advantageous.

$R_1$ and $R_2$ can form, together with the carbon atoms which carry them, an unsaturated or aromatic carbocycle or heterocyclic group.

In this case, when the carbocycle, respectively the heterocycle, is unsaturated, it is preferable for it to exhibit a single unsaturation, this unsaturation being common to the phenyl carrying the $PAr_1Ar_2$ group and to the carbocycle, respectively to the heterocycle. For this reason, the two carbons carrying the $R_1$ and $R_2$ substituents are carbons of $sp_2$ type.

The heterocycle formed by $R_1$, $R_2$ and the carbon atoms carrying $R_1$ and $R_2$ is preferably a heterocycle comprising 1 or 2 endocyclic heteroatoms.

A first group of preferred compounds is composed of the compounds of formula I.1 for which $R_1$ and $R_2$ are a hydrogen atom, a $(C_1-C_6)$alkyl (preferably methyl) group or a $(C_1-C_6)$alkoxy (preferably methoxy) group.

A second group of preferred compounds is composed of the compounds of formula I.1 for which $R_1$ and $R_2$ together form optionally substituted $(C_3-C_{11})$cycloalkenyl, optionally substituted $(C_6-C_{10})$aryl, or $(C_4-C_8)$heteroaryl comprising 1 or 2 endocyclic heteroatoms, said heteroaryl optionally being substituted.

Mention may be made, as preferred cycloalkenyl radical, of cyclic hydrocarbonaceous radicals comprising only a single ethylenic unsaturation, that is to say those in which the only $sp_2$ carbons are those carrying the $R_1$ and $R_2$ substituents.

Among this second group of preferred compounds, the compounds for which $R_1$ and $R_2$, together with the carbon atoms which carry them, form an optionally substituted phenyl radical or an optionally substituted cyclohexenyl group comprising a single unsaturation are particularly advantageous.

The following are in particular examples of the chiral body suitable for the atropisomeric diphosphine:

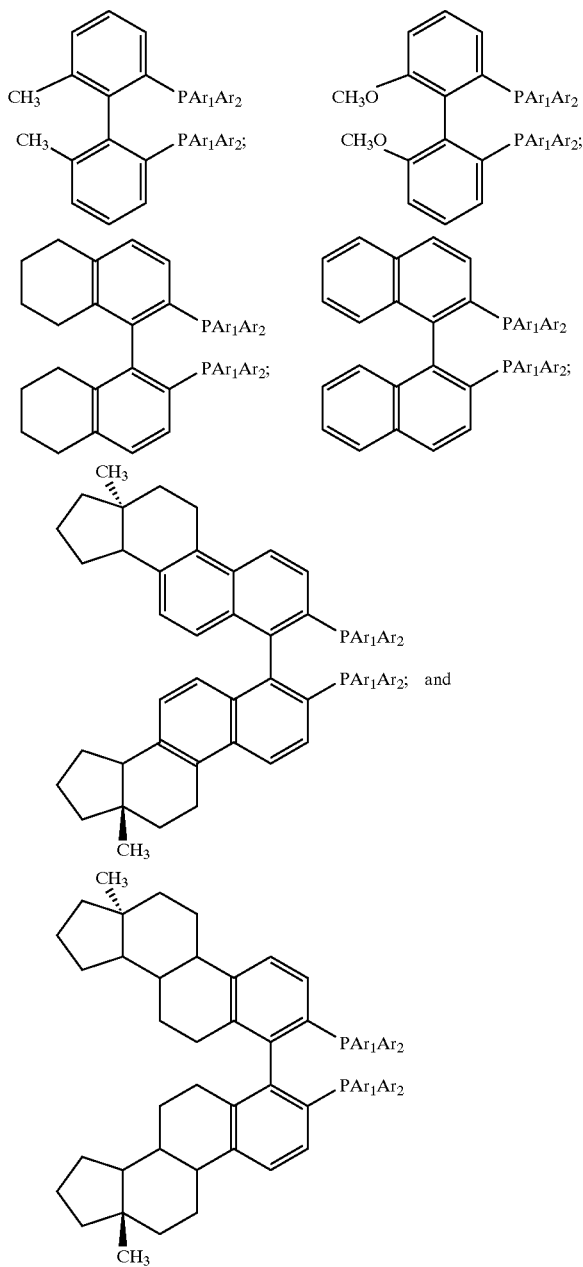

According to another embodiment of the invention, the chiral diphosphine has a chiral body corresponding to the formula:

$$R_5R_6P\text{—}A\text{—}PR_5R_6 \qquad \text{I.2.}$$

in which:

A is a divalent saturated aliphatic hydrocarbonaceous group; a divalent saturated or aromatic carbocyclic group; or a divalent saturated aliphatic hydrocarbonaceous group interrupted by a divalent saturated or aromatic carbocyclic group;

$R_5$ and $R_6$ are different and are a saturated aliphatic hydrocarbonaceous group; or an aromatic carbocyclic or aromatic heterocyclic group.

In this case, the chirality is carried by the phosphorus atoms.

It must be understood that each of the divalent groups which is A can be substituted by one or more —XZ radicals, where X and Z are as defined above. Preferably, Z is, in this case, a saturated aliphatic hydrocarbonaceous group as defined above.

The substituents of the saturated or aromatic carbocyclic and aliphatic hydrocarbonaceous groups are such that they do not disturb the $C_2$ axial symmetry of the chiral body.

The saturated aliphatic hydrocarbonaceous groups or the aromatic carbocyclic and heterocyclic groups representing $R_5$ and $R_6$ are as defined above. They can be substituted by one or more —Z or —XZ substituents in which X and Z are as defined above.

A mono- or polycyclic cycloalkylene radical is a preferred divalent saturated carbocyclic group.

The term "cycloalkylene" is understood to mean a bivalent radical corresponding to a cycloalkane in which two hydrogen atoms have been replaced by two bonds. A preferred cycloalkylene is monocyclic and corresponds to the formula:

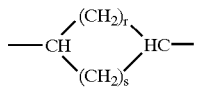

where r and s are integers from 0 to 4 where $r+s \geq 1$. Particularly preferred examples thereof are the cyclohexylene and cyclobutylene radicals, such as

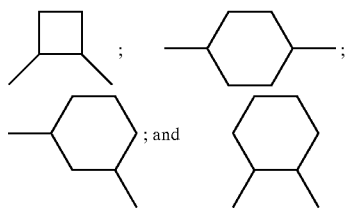

the cyclohexylene radical being the most advantageous.

A mono- or polycyclic arylene radical is a preferred divalent aromatic carbocyclic group.

The term "arylene" is understood to mean a bivalent radical corresponding to an aryl group in which two of the hydrogen atoms have been replaced by two bonds. Preferably, arylene represents phenylene and in particular ortho-phenylene and para-phenylene or a naphthylene radical, such as:

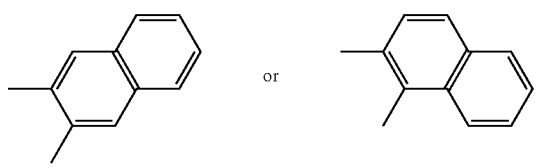

Advantageously, when $R_5$ and/or $R_6$ is a monocyclic aromatic heterocycle, the latter preferably comprises 1 to 2 endocyclic heteroatoms. Examples thereof are furyl, thienyl, imidazolyl, pyridyl or pyrrolyl.

When $R_5$ and/or $R_6$ is ($C_6$–$C_{10}$)aryl, the phenyl or naphthyl meanings, even better still the phenyl meaning, are preferred.

When $R_5$ and/or $R_6$ are alkyl, the latter is linear or branched and preferably denotes from 1 to 4 carbon atoms. Very preferably, alkyl is, in this case, methyl.

Advantageously:

A is a $C_1$–$C_6$ alkylene chain optionally substituted by one or more ($C_1$–$C_6$)alkoxy, di($C_1$–$C_6$)alkylamino or ($C_1$–$C_6$)alkylthio groups; a ($C_3$–$C_8$)cycloalkylene group optionally substituted by one or more ($C_1$–$C_6$) alkoxy, di($C_1$–$C_6$)alkylamino or ($C_1$–$C_6$)alkylthio groups; a ($C_6$–$C_{10}$)arylene group optionally substituted by one or more ($C_1$–$C_6$)alkoxy, di($C_1$–$C_6$)alkylamino or ($C_1$–$C_6$)alkylthio groups; or a —(CH$_2$)$_j$—B"—(CH$_2$)$_j$— group where j is an integer from 1 to 3 and B" is ($C_3$–$C_8$)cycloalkylene optionally substituted by one or more ($C_1$–$C_6$)alkoxy, di($C_1$–$C_6$)alkylamino or ($C_1$–$C_6$)alkylthio or ($C_6$–$C_{10}$)arylene optionally substituted by one or more ($C_1$–$C_6$)alkoxy, di($C_1$–$C_6$) alkylamino or ($C_1$–$C_6$)alkylthio;

$R_5$ and $R_6$ are different and are an aromatic monocyclic heterocycle exhibiting from 3 to 7 carbon atoms and one or more heteroatoms chosen from O, N and S; a ($C_6$–$C_{10}$)aryl group, said heterocycle and said aryl group optionally being substituted by one or more ($C_1$–$C_6$)alkyl or ($C_1$–$C_6$)alkoxy groups; or else ($C_1$–$C_6$) alkyl optionally substituted by one or more ($C_1$–$C_6$) alkoxy.

Preferably, alkylene is a branched or linear hydrocarbonaceous chain preferably comprising 1 to 4 carbon atoms.

A preferred meaning of A is —(CH$_2$)$_n$— where n is between 1 and 4, for example —CH$_2$— and more particularly the ethylene chain of formula —CH$_2$—CH$_2$—, The introduction of substituents on the $R_5$ and $R_6$ groups must be regulated by a person skilled in the art so that the $C_2$ axial symmetry is retained.

A chiral body corresponding to the formula I.2 is, for example:

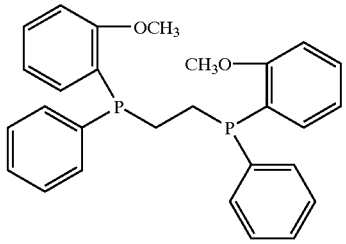

According to yet another embodiment of the invention, the chiral body of the diphosphine has the structure:

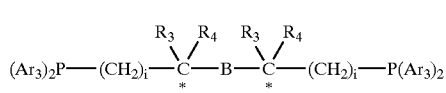

in which:

* denotes an asymmetric center;

i is 0 or 1;

$R_3$ and $R_4$ are independently a hydrogen atom or a saturated aliphatic hydrocarbonaceous group or else the $R_4$ radicals are as defined above and the $R_3$ radicals together form a divalent saturated aliphatic hydrocarbonaceous chain optionally interrupted by two X groups, X being as defined above, preferably by two identical X groups;

B is a bond or else is as defined above for A in the formula I.2;

$Ar_3$ is as defined above for $R_5$ and $R_6$ in the formula I.2.

In the case of the chiral body of formula I.3, the chirality is carried by two carbon atoms of the chain connecting the two phosphorus atoms.

According to this embodiment, the saturated aliphatic hydrocarbonaceous group is as defined above and is unsubstituted.

The divalent saturated hydrocarbonaceous chain is as defined for A above. It is preferably interrupted by two oxygen atoms or by two sulfur atoms.

Preferably:

$R_3$ and $R_4$ are selected independently from a hydrogen atom and a ($C_1$–$C_6$)alkyl group; or else the two $R_3$ groups together form a ($C_1$–$C_6$)alkylene chain optionally interrupted by two oxygen or sulfur atoms, and $R_4$ is as defined above; and $Ar_3$ is an aromatic monocyclic heterocycle exhibiting from 3 to 7 carbon atoms and one or more heteroatoms chosen from O, N and S; a ($C_6$–$C_{10}$)aryl group, said heterocycle and said aryl group optionally being substituted by one or more ($C_1$–$C_6$)alkyl or ($C_1$–$C_6$)alkoxy groups; or else ($C_1$–$C_6$)alkyl optionally substituted by one or more ($C_1$–$C_6$)alkoxy.

The alkyl and alkylene groups of the formula I.3 are linear or branched and preferably exhibit 1 to 4 carbon atoms.

When B comprises a cycloalkylene or arylene radical, the latter are such as defined above for the formula I.2.

Particularly preferred meanings of B are a bond; a ($C_1$–$C_6$)alkylene group; a ($C_6$–$C_8$)cycloalkylene group; or else a —(CH$_2$)$_p$—B'—(CH$_2$)$_q$— chain where p and q are independently an integer between 1 and 3 and B' is ($C_6$–$C_8$) cycloalkylene.

The first group of preferred compounds of formula I.3 is composed of the compounds for which $R_3$ and $R_4$ are a hydrogen atom or a methyl, ethyl, n-propyl or isopropyl group.

For a second group of preferred compounds, the two $R_3$ groups together form an alkylene chain, in which case the $R_4$ groups are ideally a hydrogen atom.

In a particularly advantageous way, the B group is chosen from:

a bond; —CH$_2$—; —CH$_2$—CH$_2$—;

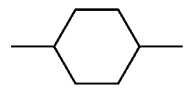

and

As regards $Ar_3$, its definition corresponds to those of $R_5$ and $R_6$ of the formula I.2. The person skilled in the art will select the preferred meanings of $Ar_3$ from those preferred in the case of the $R_5$ and $R_6$ substituents.

Examples of chiral body corresponding to the formula I.3 are as follows:

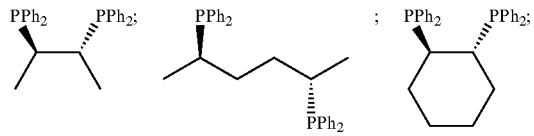

-continued

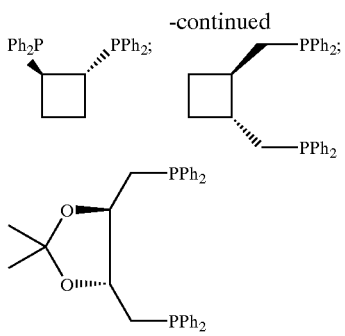

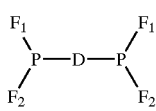

where Ph represents phenyl, or one of the enantiomeric forms of these structures.

Preferably, the chiral body can also correspond to the following formula I.4:

$$F_1 \quad F_1 \\ \diagdown P-D-P \diagup \\ F_2 \quad F_2$$
I.4 in which:
- D is as defined above for A in the formula I.2;
- $F_1$ and $F_2$ are identical and are a saturated aliphatic hydrocarbonaceous group, said group carrying at least one chiral center; a saturated carbocyclic group carrying at least one chiral center; or else
- $F_1$ and $F_2$ together form a divalent saturated aliphatic hydrocarbonaceous chain optionally interrupted by two X groups, X being as defined above, two of the carbons of said chain constituting asymmetric centers.

In the case of the compounds of formula I.4, the chirality is carried by carbon atoms of the $F_1$ and $F_2$ groups.

The substituents of the divalent groups which are D are such that they do not disturb the $C_2$ axial symmetry of the chiral body.

When $F_1$ and/or $F_2$ are a saturated aliphatic hydrocarbonaceous group or a saturated carbocyclic group, the latter are as defined above and are optionally substituted by one or more —XZ groups in which X and Z are as defined above. Preferably, Z is, in this case, a saturated aliphatic hydrocarbonaceous group as defined above.

When $F_1$ and $F_2$ together represent a divalent aliphatic hydrocarbonaceous chain interrupted by two X groups, the latter are preferably selected from O and S.

Preferably:
- D is a $C_1-C_6$ alkylene chain optionally substituted by one or more $(C_1-C_6)$alkoxy, di$(C_1-C_6)$alkylamino or $(C_1-C_6)$alkylthio groups; a $(C_3-C_8)$cycloalkylene group optionally substituted by one or more $(C_1-C_6)$ alkoxy, di$(C_1-C_6)$alkylamino or $(C_1-C_6)$alkylthio groups; a $(C_6-C_{10})$arylene group optionally substituted by one or more $(C_1-C_6)$alkoxy, di$(C_1-C_6)$alkylamino or $(C_1-C_6)$alkylthio groups; or a —(CH$_2$)$_j$—B″—(CH$_2$)$_j$— group where j and B″ are as defined above for the formula I.2;
- $F_1$ and $F_2$ are identical and are $(C_1-C_6)$alkyl optionally substituted by one or more $(C_1-C_6)$alkoxy, said alkyl group carrying at least one chiral center; $(C_3-C_8)$ cycloalkyl substituted by one or more $(C_1-C_6)$alkoxy or $(C_1-C_6)$alkyl, said cycloalkyl carrying at least one chiral center; or else $F_1$ and $F_2$ together form a $(C_1-C_6)$ alkylene chain optionally interrupted by two oxygen or sulfur atoms, said chain being substituted by one or more $(C_1-C_6)$alkyl or $(C_1-C_6)$alkoxy groups, two of the carbons of said chain constituting asymmetric centers.

The alkylene chains and the alkyl radicals of the alkyl, alkoxy, alkylthio and dialkylamino groups preferably comprise 1 to 4 carbon atoms.

When D comprises cycloalkylene or arylene, the latter are as defined above for the formula I.2.

The substituents of the alkylene, cycloalkylene and arylene groups are such that they do not disturb the $C_2$ axial symmetry of the chiral body.

In a particularly advantageous way, $F_1$ and $F_2$, together with the phosphorus atom which carries them, form a five- or six-membered ring substituted by two identical radicals selected from $(C_1-C_6)$alkyl and $(C_1-C_6)$alkoxy. Preferably, the five- or six-membered ring is a heterocycle comprising the phosphorus atom as sole heteroatom.

A meaning of $F_1$ and $F_2$ which is also preferred is the menthyl radical and in particular the 2-isopropyl-5-methylcyclohexyloxy radical.

Advantageously, the chiral body of formula I.4 has the structure

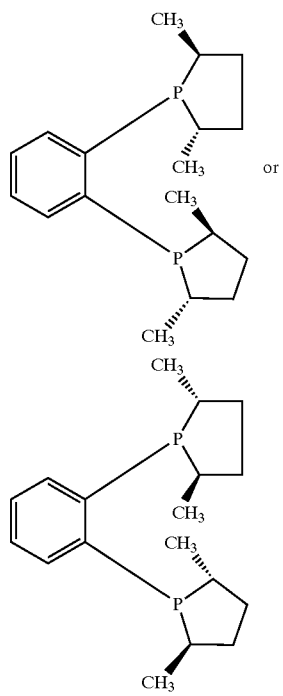

According to another embodiment of the invention, the chiral body has either of the following formulae I.5 or I.6:

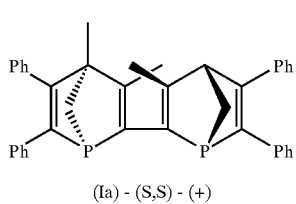

(Ia) - (S,S) - (+)

-continued

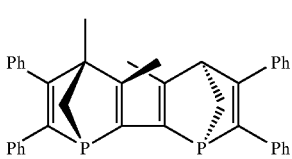

(Ib) - (R,R) - (-)

These compounds and their methods of preparation are disclosed in particular in Application R 94 167.

According to yet another embodiment, the chiral body has, for formula, the formula I.7:

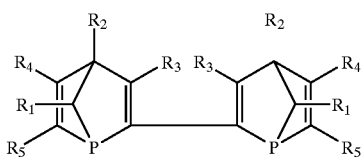

in which:

R$_1$, R$_2$, R$_3$, R$_4$ and R$_5$, which are identical or different, are a hydrogen atom or an optionally substituted hydrocarbonaceous radical having from 1 to 40 carbon atoms which can be a saturated or unsaturated and linear or branched acyclic aliphatic radical; a saturated, unsaturated or aromatic and monocyclic or polycyclic carbocyclic or heterocyclic radical; a saturated or unsaturated and linear or branched aliphatic radical carrying a cyclic substituent, R$_2$ and R$_3$ can form, together with the carbon atoms which carry them, a saturated or unsaturated ring, R$_5$ can be a radical of type

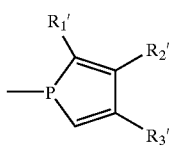

in which R$_1$', R$_2$' and R$_3$' have the same meaning as that given for R$_1$, R$_2$ and R$_3$, R$_4$ and R$_5$ cannot simultaneously be a phenyl group.

These compounds and their methods of preparation are disclosed in Application R 97 014.

Examples of diphosphines corresponding to I.7 above are more specifically the following:

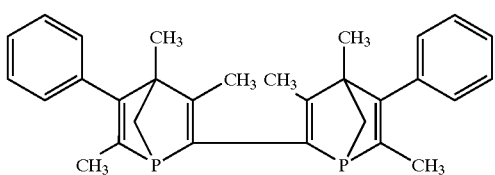

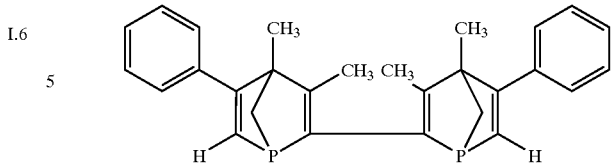

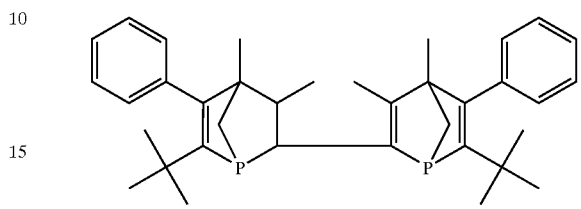

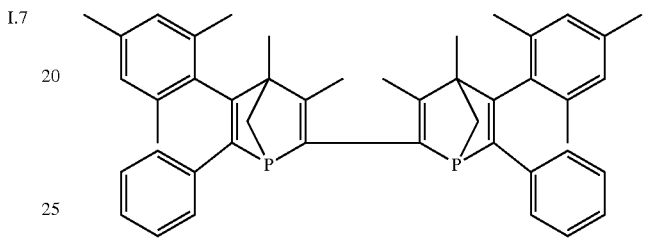

The above formulae I.1 to I.7 are given by way of illustration but the invention is not limited to these specific structures for the chiral body of the diphosphine.

It is essential according to the invention for the chiral body of the diphosphine to carry two functional groups capable of reacting with the polymerizable monomers.

The identicalness of these two functional groups is necessary in order to ensure the C$_2$ axial symmetry of the molecule. The nature of these functional groups is not critical according to the invention.

The choice of these functional groups, combined with the choice of the polymerizable monomers, determines the nature of the resulting polymer.

Examples of functional groups are the amino, halogen, hydroxyl, thiol, carboxyl, isocyanate and thioisocyanate groups.

The present invention encompasses all types of polymers and in particular linear polymers, such as polyester, polyamide, polyurea, polythiourea, polyimide, polycarbonate, polyterephthalate and polysulfone.

Although the invention is not intended to be specifically limited thereto, polyamides, polyureas, polythioureas and polyimides will form the subject of a more detailed description.

According to the invention, preference is given to the polymers resulting from the polymerization of a chiral diphosphine with a single polymerizable monomer.

The polyureas, polyamides, polythioureas and polyimides of the invention can be prepared starting from a chiral diphosphine composed of a chiral body carrying, as functional groups, two amino groups or two aminomethyl groups. The incorporation of these amino or aminomethyl groups can be carried out in any way, the method used to do this not being crucial according to the invention.

By way of illustration, the preparation of the diphosphines of formula II:

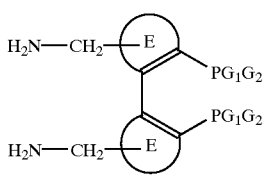

in which:

E is phenyl or naphthyl; and $G_1$ and $G_2$ are independently a saturated or aromatic carbocyclic group, is described below.

According to this definition, phenyl and naphthyl are optionally substituted.

The carbocyclic radicals are generally as defined above. They can be substituted.

The carbocyclic radicals exhibit, in the case of $G_1$ and/or $G_2$, a saturated and/or aromatic part.

The substituents of the phenyl, naphthyl and carbocyclic radicals of the above formula II are inert under the conditions of implementation of the process for the preparation of the compounds II.

Preferably, these substituents are alkyl or alkoxy (for example, $C_1$–$C_{25}$, $C_1$–$C_{12}$ or $C_1$–$C_6$).

Advantageously:

E is phenyl or naphthyl, optionally substituted by one or more radicals selected from ($C_1$–$C_6$)alkyl and ($C_1$–$C_6$) alkoxy; and $G_1$ and $G_2$ are independently a phenyl group optionally substituted by one or more ($C_1$–$C_6$)alkyl or ($C_1$–$C_6$) alkoxy; or a ($C_4$–$C_8$)cycloalkyl group optionally substituted by one or more ($C_1$–$C_6$)alkyl groups, is described below.

The compound of formula II is easily obtained by reduction, by means of a reducing agent, of the corresponding nitrile of formula III below:

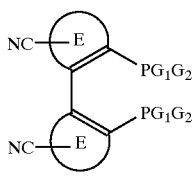

where $G_1$, $G_2$ and E are as defined above.

An appropriate reducing agent is lithium aluminum hydride (LiAlH$_4$).

The reaction is preferably carried out in a solvent or a mixture of solvents.

When the reducing agent is LiAlH$_4$, the solvent advantageously comprises one or more aromatic hydrocarbons (such as benzene, toluene and xylene) as a mixture with one or more ethers.

Mention may be made, as ether, of $C_1$–$C_6$ alkyl ethers (diethyl ether and diisopropyl ether), cyclic ethers (dioxane, tetrahydrofuran), dimethoxyethane and diethylene glycol dimethyl ether.

When the reducing agent is LiAlH$_4$, the decision will more preferably be taken to opt for a mixture of toluene and tetrahydrofuran in proportions varying between (v/v) 70–50/30–50:toluene/tetrahydrofuran (for example 60/40:toluene/THF).

The reduction can be carried out at a temperature of between 20° C. and 100° C., preferably between 40° C. and 80° C.

A large excess of the reducing agent will generally be used. Thus, the molar ratio of the reducing agent to the compound of formula III generally varies between 1 and 30, for example between 2 and 20, in particular between 5 and 18.

The concentration of the reactants in the medium is variable; it can be maintained between 0.005 and 1 mol/l.

The nitrites of formula III can be prepared simply by carrying out the following stages i) to iv):

i) first of all, a diol of formula IV:

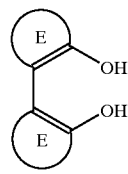

in which E is as defined above, is brominated by means of an appropriate brominating agent, so as to obtain a dibrominated compound of formula V:

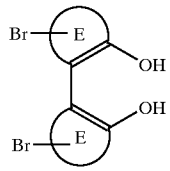

in which E is as defined above:

ii) the compound of formula V obtained in the preceding stage is esterified by reaction with a sulfonic acid or an activated form of the latter, so as to obtain the corresponding disulfonate;

iii) the two bromine atoms are subsequently substituted by cyano groups by reaction of the disulfonate obtained in the preceding stage with an appropriate nucleophilic agent, so as to obtain the corresponding nitrile;

iv) coupling of a phosphine of formula VI:

in which X' is a hydrogen atom or a halogen atom and $G_1$ and $G_2$ are as defined above, with the nitrile obtained in the preceding stage in the presence of a catalyst based on a transition metal, so as to obtain the expected compound of formula III.

In stage i), the phenyl nucleus, respectively the naphthyl nucleus, of the diol of formula IV is brominated by reaction with an appropriate brominating agent.

The hydroxyl groups present on the naphthyl nuclei, respectively phenyl nuclei, direct the electrophilic reaction so that the position of the bromine atoms on these nuclei is well determined.

When E is an unsubstituted phenyl nucleus or a phenyl nucleus carrying, in the meta position with respect to the OH group, a substituent such as ($C_1$–$C_6$)alkyl or ($C_1$–$C_6$)alkoxy, the corresponding diol of formula IVa:

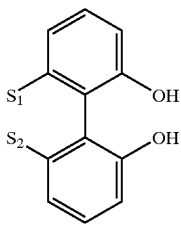

IVa where $S_1$ and $S_2$ are independently inert substituents, selected in particular from a hydrogen atom or an alkyl or alkoxy group, preferably a $C_1$–$C_6$ group, results in the corresponding brominated compound of formula Va:

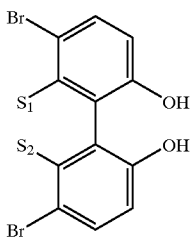

Va

When E is a naphthyl nucleus, the bromination of the corresponding diol of formula IVb:

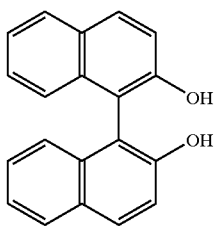

IVb results in the following compound Vb:

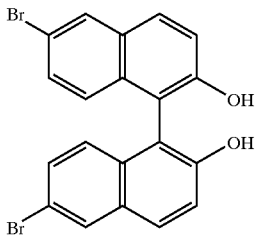

Vb

The bromination reaction of the phenyl or naphthyl nuclei is an elecrophilic reaction which is easily carried out by reaction of $Br_2$ with the corresponding diol.

This reaction can be carried out in the presence of a catalyst, such as a Lewis acid and in particular iron chloride. However, in so far as the hydroxyl groups present on the phenyl and naphthyl nuclei activate these nuclei, the bromination is easily carried out in the absence of any catalyst.

The diols of formula IV are so reactive that it is desirable to carry out the bromination at low temperature, for example between −78° C. and −30° C., preferably between −78° C. and −50° C.

According to a preferred embodiment of the invention, the bromination takes place in an inert aprotic solvent, such as an aromatic hydrocarbon (for example chlorobenzene and dichlorobenzene); a nitrated aromatic hydrocarbon, such as a nitrobenzene; an optionally halogenated aliphatic hydrocarbon, such as hexane, heptane, methylene chloride, carbon tetrachloride or dichloroethane; or an aliphatic hydrocarbon.

Generally, aromatic hydrocarbons exhibiting aromatic nuclei depleted in electrons, that is to say carrying one or more electron-withdrawing substituents, can be used.

Mention may be made, as preferred solvent, of halogenated aliphatic hydrocarbons and in particular methylene chloride.

In an alternative form, it is possible to carry out the reaction in glacial acetic acid as solvent. Under these conditions, a solution of bromine in acetic acid is generally added dropwise to a solution of the diol IV in acetic acid.

Whether or not the reaction is carried out in the presence of acetic acid, an excess of the brominating agent with respect to the diol IV is used.

Preferably, the molar ratio of the brominating agent to the diol IV varies between 2 and 5, better still between 2 and 3.

When the reaction is carried out in solution, the concentration of the reactants can vary very widely between 0.01 and 10 mol/l, for example between 0.05 and 1 mol/l.

In stage (ii), the hydroxyl functional groups of the diol V are esterified by reaction with a sulfonic acid or an activated form of the latter, so as to obtain the corresponding disulfonate.

According to the invention, the nature of the sulfonic acid used is not determining per se.

The sulfonic acid advantageously has the formula:

$$P\text{—}SO_2\text{—}OH$$

where P is an aliphatic hydrocarbonaceous group; an aromatic carbocyclic group; or an aliphatic group substituted by an aromatic carbocyclic group.

The term "aliphatic hydrocarbonaceous group" is understood to mean in particular an optionally substituted alkyl group as defined above. The nature of the substituent is such that the latter does not react under the conditions of the esterification reaction. A preferred example of alkyl group substituent is a halogen atom, such as fluorine, chlorine, bromine or iodine.

The term "aromatic carbocyclic group" is understood to mean mono- or polycyclic aromatic groups and in particular the mono-, bi- or tricyclic groups defined above, for example phenyl, naphthyl, anthryl or phenanthryl.

The aromatic carbocyclic group is optionally substituted. The nature of the substituent is not critical, provided that the latter does not react under the esterification conditions. The substituent is advantageously optionally halogenated alkyl, alkyl being as defined above and halogen being chlorine, fluorine, bromine or iodine, preferably chlorine. By way of example, optionally halogenated alkyl denotes perfluoroalkyl, such as trifluoromethyl or pentafluoroethyl.

According to a preferred embodiment of the invention, is ($C_6$–$C_{10}$)aryl optionally substituted by one or more optionally halogenated ($C_1$–$C_6$)alkyl; optionally halogenated ($C_1$–$C_6$)alkyl; or ($C_6$–$C_{10}$)aryl($C_1$–$C_6$)alkyl in which the aryl group is optionally substituted by one or more optionally halogenated ($C_1$–$C_6$)alkyl and the alkyl group is optionally halogenated.

Appropriate examples of such sulfonic acids are paratoluenesulfonic acid, methanesulfonic acid and trifluoromethanesulfonic acid, the latter being more particularly preferred.

According to a preferred embodiment of the invention, an activated derivative of the sulfonic acid is used. The term "activated derivative" denotes a sulfonic acid in which the —SO₃H acidic functional group is activated, for example by formation of an anhydride bond or of the —SO₂Cl group.

A particularly advantageous sulfonic acid derivative is the symmetrical anhydride of trifluoromethanesulfonic acid, of formula (CF₃—SO₂)₂O.

When the sulfonic acid used has the above formula P—SO₃H or is an activated form of this acid, the disulfonate obtained on conclusion of stage ii) corresponds to the formula VII:

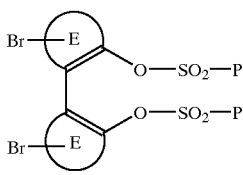

VII in which E and P are as defined above.

The conditions of the esterification reaction will be easily developed by a person skilled in the art. These conditions depending in particular on the nature of the esterification agent. When the esterification agent is a sulfonic acid, a higher reaction temperature, of between 20 and 100° C., may prove to be necessary. Conversely, starting from an activated form of this acid, such as an anhydride or a sulfonyl chloride, a lower temperature may be suitable. Generally, a temperature of between −30° C. and 50° C., preferably between −15 and 20° C., may suffice in this case.

The esterification is preferably carried out in a solvent. Appropriate solvents are in particular optionally halogenated aliphatic, aromatic or cyclic hydrocarbons, such as those defined above. Mention may be made of carbon tetrachloride and dichloromethane. Dichloromethane is particularly preferred. Ethers can also be used as solvent. Mention will be made, for example, of di($C_1$–$C_6$ alkyl)ethers (diethyl ether and diisopropyl ether), cyclic ethers (tetrahydrofuran and dioxane), dimethoxyethane and diethylene glycol dimethyl ether.

When the esterification agent is other than trifluoromethanesulfonic acid, it is desirable to introduce a base into the reaction medium. Examples of base are N-methylmorpholine, triethylamine, tributylamine, diisopropylethylamine, dicyclohexylamine, N-methylpiperidine, pyridine, 2,6-dimethylpyridine, 4-(1-pyrrolidinyl)pyridine, picoline, 4-(N,N-dimethylamino) pyridine, 2,6-di(t-butyl)-4-methylpyridine, quinoline, N,N-dimethylaniline and N,N-diethylaniline.

Pyridine and 4-dimethylaminopyridine will essentially be selected as preferred bases.

The reaction can also be carried out in a two-phase mixture of water and an organic solvent, such as a halogenated aliphatic hydrocarbon (for example carbon tetrachloride). In this case, it is preferable to use an esterification agent in the anhydride form and to carry out the reaction in the presence of a water-soluble base, such as KOH, NaOH or $K_2CO_3$, preferably KOH.

The reaction of the sulfonic acid or its activated derivative with the brominated diol V is stoichiometric. Nevertheless, it is preferable to carry out the reaction in the presence of an excess of the acid or its activated form. Thus, a ratio of the acid, optionally in the activated form, to the diol V of between 2 and 5, better still between 2 and 3, is recommended.

When the reaction is carried out in solution, the concentration of the reactants, which is not a critical parameter according to the invention, can vary between 0.1 and 10 mol/l, advantageously between 1 and 5 mol/l.

A person skilled in the art may draw inspiration from the operating conditions illustrated in J. Org. Chem., Vol. 58, No. 7, 1993, 1945–1948, and Tetrahedron Letters, Vol. 31, No. 7, 985–988, 1990, for the implementation of the esterification.

The following stage (iii) is a nucleophilic substitution. The two bromine atoms carried by the E nuclei are displaced by cyano groups by reaction with an appropriate nucleophilic agent.

A person skilled in the art may use any one of the methods known in the art so as to carry out this substitution.

According to a preferred embodiment of the invention, the nucleophilic agent used is copper cyanide.

The molar ratio of the copper cyanide to the compound VI is preferably greater than 2, it can advantageously vary between 2 and 4, preferably between 2 and 3.

The reaction is preferably carried out in a solvent. Mention may be made, as example of solvents, of amides, such as formamide, dimethylformamide, dimethylacetamide, N-methyl-2-pyrrolidinone and hexamethylphosphoramide. Dimethylformamide is clearly preferred. Pyridine is also an appropriate solvent. The temperature of the reaction is advantageously maintained between 50 and 200° C., better still between 80 and 180° C.

The concentration of the reactants in the reaction medium generally oscillates between 0.1 and 10 mol/l, for example between 2 and 7 mol/l.

The isolation of the nitrile involves the decomposition of the intermediate complex formed and the trapping of the excess cyanide.

The hydrolysis of the intermediate complex can be carried out either by the action of iron chloride hydrate or by the action of aqueous ethylenediamine.

In the first case, the reaction medium is poured into a 50–80% (g/ml) aqueous iron chloride solution comprising concentrated hydrochloric acid. The resulting solution is heated at 40–80° C. until the complex has completely decomposed. The medium is then separated by settling and extracted in a conventional way.

In the second case, the reaction medium is poured into an aqueous ethylenediamine solution (ethylenediamine/water: 1/5–1/1 (v/v), for example 1/3) and then the combined mixture is vigorously stirred. The medium is then separated by settling and extracted in a way known per se.

A person skilled in the art may draw inspiration from the studies by L. Friedman et al., published in J.O.C., 1961, 26, 1522, in isolating the nitrile.

Starting from the disulfonate of formula VII mentioned above, the product obtained on conclusion of this stage is the nitrile of formula VIII:

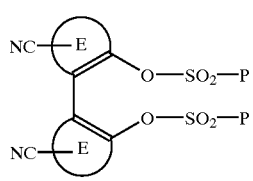

VIII in which E and P are as defined above and the position of the cyano group on the E nucleus is the same as that of the bromine in the compound VII.

In stage (iv), the reaction is carried out with a crossed coupling of a diphosphine of formula VI:

$$X'PG_1G_2 \qquad VI$$

in which X' is a halogen or hydrogen atom and $G_1$ and $G_2$ are as defined above, with the nitrile obtained in the preceding stage in the presence of a catalyst based on a transition metal.

This coupling results directly in the expected compound of formula III.

Examples of appropriate catalysts are catalysts based on nickel, palladium, rhodium, ruthenium, platinum or a mixture of these metals.

The preferred catalysts are nickel-based catalysts, such as those selected from $NiCl_2$; $NiBr_2$; $NiCl_2(dppp)$; $NiCl_2(dppb)$; $NiCl_2(dppf)$; $NiCl_2(dppe)$; $NiCl_2(PPh_3)_2$; $Ni(CO)_2(PPh_3)_2$; $Ni(PPh_3)_4$ and $Ni[P(PhO)_3]_4$ where dppe means (diphenylphosphino)ethane, dppp means (diphenylphosphino)propane, dppb means (diphenylphosphino)butane and dppf means (diphenylphosphino)ferrocenyl.

Preference is given, among these catalysts, to $NiCl_2$(dppe).

The reaction is generally carried out at a temperature of 50 to 200° C., preferably of 80 to 130° C.

The molar ratio of the compound VI to the nitrile is at least 2. It generally varies between 2 and 4, for example between 2 and 3.

The amount of catalyst is preferably such that the molar ratio of the compound of formula VII to the catalyst varies between 5 and 100, in particular between 5 and 80.

The reaction is preferably carried out in a polar aprotic solvent and in particular an amide, such as those mentioned above. Here again, N,N-dimethylformamide is preferred. Other types of polar solvents can nevertheless be used, such as $(C_1-C_6)$alkanols (ethanol), aromatic hydrocarbons (toluene, xylene and benzene), ethers (dioxane) and acetonitrile.

The precise reaction conditions depend on the nature of the compound of formula VI involved in the reaction.

When the compound VI is $HPG_1G_2$, the reaction is advantageously carried out in the presence of a base.

Bases which are particularly well suited are pyridine, 4-dimethylaminopyridine, 2,6-di(tert-butyl)pyridine, 1,8-diazobicyclo[5.4.0]undec-7-ene (DBU), 1,5-diazabicyclo[4.3.0]non-5-ene (DBN) and 1,4-diazabicyclo[2.2.2]octane (DABCO or triethylene-diamine). Use will advantageously be made of DABCO as base. In this case, it is preferable for the molar ratio of the nitrile to the catalyst to be between 5 and 20, for example between 7 and 15.

When the compound of formula VI is $halPG_1G_2$, where hal is a halogen atom, preferably Cl or Br (better still Cl), it is necessary to add zinc to the reaction medium.

The amount of zinc is preferably such that the molar ratio of the zinc to $halPG_1G_2$ varies between 1 and 2, preferably between 1.2 and 1.7.

In this case, it is desirable to cool the reaction mixture comprising the solvent, the nitrile and the compound VI to a temperature of between −10 and 20° C. throughout the addition of the zinc to the reaction medium. The reaction then takes place by heating to an appropriate temperature of between 50 and 200° C.

When the compound of formula VI is $halPG_1G_2$, it is preferable for the molar ratio of the nitrile to the catalyst to be between 40 and 80, for example between 50 and 70.

For further details on the implementation of these coupling reactions, a person skilled in the art will refer to D. Cai et al., J.O.C., 1994, 59, 7189, and D. J. Ager et al., Chem. Comm., 1997, 2359.

Thus, when E is optionally substituted phenyl, preferably substituted by $(C_1-C_6)$alkyl or $(C_1-C_6)$alkoxy, the compound obtained on conclusion of stage (iv) has the formula IIIa:

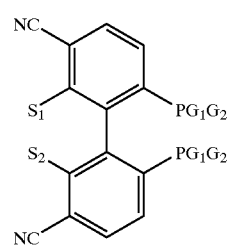

in which $G_1$, $G_2$, $S_1$, and $S_2$ are as defined above for the formula IVa.

When E is naphthyl, the compound obtained on conclusion of stage (iv) has the formula IIIb:

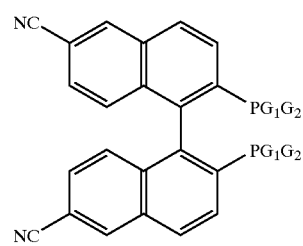

in which $G_1$ and $G_2$ are as defined above.

In the case where the diphosphine exhibits a structure distinct from the above formula II, a person skilled in the art will use his basic knowledge of organic chemistry to carry out this synthesis from commercially available products.

Generally, the introduction of aminomethyl groups onto the chiral body can be carried out by conversion to aminomethyl groups of methyl substituents suitably positioned on an appropriate chiral body.

To do this, first of all the bromination of the methyl substituents of a starting dimethylated compound might be carried out by reaction with an appropriate brominating agent and then nucleophilic substitution of the bromine atoms thus introduced might be carried out by reaction with appropriate primary or secondary amines, so as to be able to easily regenerate an —$NH_2$ group. An example of such an amine is in particular benzylamine, which, after nucleophilic reaction, can be easily subjected to a reaction for debenzylation by catalytic hydrogenation.

Another method consists in carrying out the bromination of the methyl substituents, followed by the reaction of the corresponding brominated derivatives with $NaN_3$ and then reduction by catalytic hydrogenation or the action of an appropriate reducing agent.

In an alternative form, it is possible to envisage the bromination of the methyl substituents, followed by the reaction with an alkali metal phthalimide and then hydrolysis of the resulting compound.

It must be understood that, when the starting dimethylated compound comprises one or more sensitive functional groups which are thus reactive under oxidizing conditions, it is advisable to protect them beforehand. Thus, when the starting dimethylated compound comprises a phosphorus atom, the latter is protected beforehand, for example by oxidation.

When the target polymer is a polyurea, the latter can be synthesized by polymerization of a diphosphine carrying two —NH$_2$ or —CH$_2$—NH$_2$ groups with one or more diisocyanates.

The nature of the diisocyanate is not critical per se. The diisocyanate is preferably a diisocyanate of formula IX:

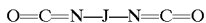

O=C=N—J—N=C=O    IX in which J is a divalent hydrocarbonaceous radical with an aliphatic, alicyclic and/or aromatic nature. The size of the J radical will be adjusted by a person skilled in the art according to the final use of the ligand and in particular according to the reaction which has to be catalyzed by the metal complex formed from this polymer ligand.

The catalytic sites of the polymer of the invention are situated in the units resulting from the diphosphine. The size of the J radical thus determines the spacing of the catalytic sites.

The J radical is, for example, a $C_1$–$C_{16}$, preferably $C_1$–$C_{12}$, alkylene chain optionally interrupted by one or more (preferably 1 to 4, better still 1 to 2) heteroatoms chosen from O, N and S, said chain optionally comprising one or more unsaturations (preferably 1 to 4, better still 1 to 2); a —(CH$_2$)$_a$—K—(CH$_2$)$_b$— radical, where a and b are independently an integer from 0 to 6 and K is ($C_6$–$C_8$) cycloalkylene; a —(CH$_2$)$_a$—L—(CH$_2$)$_b$— radical, where a and b are as defined above and L is ($C_{6-10}$)arylene; a —(CH$_2$)$_a$—V$_o$—(CH$_2$)$_b$— radical, where a and b are as defined above and V$_o$ is 5- to 8-membered heteroarylene comprising 1 to 3 heteroatoms selected from O, N and S; or else an —M$_o$—Q—M$_o$— radical in which M$_o$ is selected from ($C_3$–$C_8$)cycloalkylene and ($C_6$–$C_{10}$)arylene and Q is a bond, a sulfur atom, an oxygen atom, ($C_1$–$C_4$)alkylene, —SO—, —SO$_2$— or —CO—.

When J comprises an alkylene chain, the latter is linear or branched and preferably comprises 1 to 6 carbon atoms. When this alkylene chain comprises a nitrogen atom, the latter carries a ($C_1$–$C_6$)alkyl radical or a hydrogen atom.

When J comprises cycloalkylene, it is preferable for J to be cyclohexylene.

When J comprises arylene, it is preferable for J to be phenylene or naphthalene.

When J is —(CH$_2$)$_a$—L—(CH$_2$)$_b$—, —(CH$_2$)$_a$—K—(CH$_2$)$_b$— or —(CH$_2$)$_a$—V$_o$—(CH$_2$)$_b$—, it is preferable for a and b to identical.

The term "heteroarylene" is understood to mean a bivalent radical corresponding to a heterocycle in which two hydrogen atoms have been replaced by two bonds.

Preference is given to the heteroarylenes derived from the heterocycles: furan, thiophene, pyrrole, oxazole, thiazole, imidazole, pyrazole, isoxazole, isothiazole, pyridine, pyridazine, pyrimidine, pyrazine, indolizine, indole, isoindole, benzofuran, benzothiophene, benzimidazole, benzothiazole, quinoline, isoquinoline, cinnoline, phthalazine, quinazoline, naphthyridine and pteridine. In a highly advantageously way, heteroarylene is derived from imidazole, benzimidazole, pyrimidine or quinazoline.

When J is —M$_o$—Q—M$_o$—, it is preferable for Q to be ($C_1$–$C_2$)alkylene or a bond and for M$_o$ to be cyclohexylene or phenylene.

The J radical as defined above can carry one or more substituents selected from a halogen atom, a $C_1$–$C_6$ alkyl group, a $C_1$–$C_6$ alkoxy group, an oxo group and a di($C_1$–$C_6$) alkylamino group.

Examples of diisocyanates which are particularly appropriate are:

1,2-diisocyanatopropane;
1,2-diisocyanatobutane;
1,3-diisocyanatobutane;
2,4-diisocyanatotoluene;
4,4'-diisocyanato-3,3',5,5'-tetraethyldiphenylmethane;
1,5-diisocyanatohexane; and
5-isocyanato-1-isocyanatomethyl-1,3,3-trimethylcyclohexane.

Preference is given, among the diisocyanates preferably used according to the invention, to those exhibiting a $C_2$ axis of symmetry or a plane of symmetry.

A particularly preferred group of diisocyanates is composed in particular of the following compounds, which exhibit $C_2$ axial symmetry;

1,12-diisocyanatododecane
1,8-diisocyanatooctane
trans-1,4-cyclohexane diisocyanate
2,6-diisocyanatotoluene
2,3-diisocyanatoxylene
2,6-diisocyanatoxylene
3,3'-diisocyanatobiphenyl
4,4'-diisocyanatobiphenyl
3,3'-diisocyanatodiphenylmethane
4,4'-diisocyanatodiphenylmethane
1,6-diisocyanatohexane
1,3-diisocyanatobenzene
1,4-diisocyanatobenzene
2-methyl-1,3-phenylene diisocyanate
4-methyl-1,3-phenylene diisocyanate
1,3-phenylene diisocyanate
4,4'-diisocyanato-3,3'-dimethyldiphenyl
4,4'-diisocyanato-3,3'-dimethyldiphenylmethane
4,4'-diisocyanatodiphenylethane
3,3'-diisocyanatodiphenyl ether
4,4'-diisocyanatodiphenyl ether
3,3'-diisocyanatodiphenyl sulfone
4,4'-diisocyanatodiphenyl sulfone
3,3'-diisocyanatobenzophenone
4,4'-diisocyanatobenzophenone
3,3'-diisocyanatodicyclohexylmethane
4,4'-diisocyanatodicyclohexylethane
1,5-diisocyanatonaphthalene
4,4'-diisocyanato-3,3'-dichlorobiphenyl
4,4'-diisocyanato-3,3'-dimethoxybiphenyl.

More particularly, the following diisocyanates with $C_2$ axial symmetry are preferred:

1,6-diisocyanatohexane
2,6-diisocyanatotoluene
2,4-diisocyanatoxylene
4,4'-diisocyanatobiphenyl
4,4'-diisocyanatodiphenylmethane
4,4'-diisocyanatodiphenyl ether
4,4'-diisocyanatobiphenyl sulfone
4,4'-diisocyanatobenzophenone
4,4'-diisocyanatodicyclohexylethane
1,5-diisocyanatonaphthalene.

The condensation of the diisocyanate with the diphosphine is carried out under appropriate conditions which are easily determined by a person skilled in the art.

These polymerization conditions are preferably adjusted so as to obtain a polymer exhibiting a degree of polymerization of 2 to 100, preferably of 5 to 100, for example of 2 to 50, better still of 4 to 25.

Polyureas with a degree of polymerization of 3 to 8 are particularly well suited.

A person skilled in the art will choose the degree of polymerization so that the resulting polymer is insoluble in the solvent or mixtures of solvents used in the asymmetric reaction which has to be catalyzed.

The choice of the polymerization method is not critical according to the invention.

A particularly appropriate method is solution polymerization.

The solvent is generally a polar aprotic solvent selected from an optionally halogenated aliphatic hydrocarbon, for example methylene chloride, chloroform, carbon tetrachloride or dichloroethane; an optionally halogenated aromatic hydrocarbon, for example chlorobenzene or dichlorobenzene; an ether, such as diethyl ether, diisopropyl ether, tetrahydrofuran, dioxane, diethylene glycol dimethyl ether or glymes, in particular 1,2-dimethoxyethane; an amide, such as formamide, dimethylformamide, dimethylacetamide, N-methyl-2-pyrrolidinone or hexamethylphosphoramide; a nitrile, such as acetonitrile or isobutyronitrile; and dimethyl sulfoxide.

The concentration of the reactants in the solution varies very widely according to the solubility of the reactants. It is generally between 0.05 and 1 mol/l, preferably between 0.01 and 1 mol/l, for example 0.1 mol/l.

The diisocyanate is preferably used in excess with respect to the diphosphine, although, if absolutely necessary, a stoichiometric ratio of these two compounds may be suitable.

Thus, the molar ratio of the diisocyanate to the diphosphine is generally set between 1 and 1.5, for example between 1 and 1.3.

The temperature at which the polymerization is carried out is determined according to the reactivity of the various reactants and the degree of polymerization desired. By way of indication, the temperature varies between −20° C. and 100° C., preferably between ambient temperature and 100° C., for example between 15 and 100° C., better still between 15 and 40° C. It is advantageously 20° C.

The polymerization is carried out conventionally by dissolving the reactants in the solvent, mixing, optionally heating the reaction medium and then isolating the polymer, for example by filtering the reaction medium. It should be noted that it may be necessary, before isolation of the polymer, to deactivate the ends of the polymer chain, in particular unreacted isocyanate functional groups, by addition of a $C_1$–$C_6$ alkanol, for example propanol, isopropanol, methanol, ethanol or even tert-butyl alcohol.

When the polymer is a polyamide, the latter can be prepared by condensing a chiral diphosphine carrying two amino or aminomethyl functional groups with one or more dicarboxylic acids or activated derivatives of the latter.

The dicarboxylic acid advantageously corresponds to the following formula X:

HOOC—M—COOH    X in which M is as defined for J above. The preferred meanings of J indicated above are also preferred meanings of M. The M radical can be substituted by one or more halogen atoms or oxo, $(C_1$–$C_6)$alkyl, $(C_1$–$C_6)$alkoxy or di$(C_1$–$C_6)$ alkylamino groups.

Preference is given, among these dicarboxylic acids, to those exhibiting a $C_2$ axis of symmetry, such as:
the aliphatic acids selected from:

malonic acid
succinic acid
glutaric acid
adipic acid
2,4-dimethyladipic acid
pimelic acid
suberic acid
azelaic acid
sebacic acid
dodecanedioic acid
fumaric acid
maleic acid
methyliminodiacetic acid
3-(dimethylamino)hexanedioic acid, cycloalkanedicarboxylic acids and in particular:

cyclohexane-1,4-dicarboxylic acid the aromatic dicarboxylic acids selected from:

phthalic acid
isophthalic acid
terephthalic acid
phenylenediacetic acid
naphthalene-1,5-dicarboxylic acid
diphenyl-4,4'-dicarboxylic acid
diphenyl-3,3'-dicarboxylic acid
4,4'-dicarboxydiphenyl sulfone
3,3'-dicarboxydiphenyl sulfone.

Other dicarboxylic acids can nevertheless be used, such as, for example:

3-(dimethylamino)cyclopentane-1,2-dicarboxylic acid
naphthalene-1,6-dicarboxylic acid
pyrimidinedicarboxylic acids; and
imidazoledicarboxylic acids.

A particularly preferred group of dicarboxylic acids is composed of the following acids:

succinic acid
adipic acid
fumaric acid
isophthalic acid
terephthalic acid
naphthalene-1,5-dicarboxylic acid
diphenyl-4,4'-dicarboxylic acid
diphenyl-3,3 1-dicarboxylic acid.

The activated derivative of the dicarboxylic acid more generally denotes the dicarboxylic acid compound in which one or both carboxylic functional groups have been modified so as to increase their reactivity.

Activated derivatives of dicarboxylic acid are, for example, obtained by formation of an anhydride bond or of a —COY group, where Y is a halogen atom, such as bromine or chlorine.

Other activated derivatives of dicarboxylic acids are those carrying, instead of and in place of the carboxylic functional groups, —COT groups, where T denotes an azide, imidazolide, p-nitrophenoxy, 1-benzotriazole, N—O- succinimide, acyloxy (such as pivaloyloxy), ($C_1$–$C_4$ alkoxy) carbonyloxy, or dialkyl- or dicycloalkyl-O-ureide group.

An example of a polymer which is particularly preferred is a polymer exhibiting, as repeat unit:

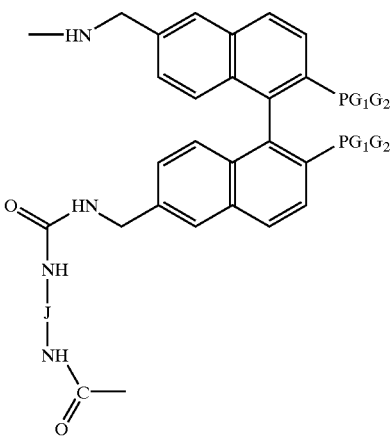

in which

G₁ and G₂ are independently a saturated or aromatic carbocyclic group; and

J is a divalent hydrocarbonaceous radical with an aliphatic, alicyclic and/or aromatic nature;

the degree of polymerization preferably being between 2 and 100, better still between 2 and 50.

Another example of a polymer which is preferred is a polymer exhibiting, as repeat unit:

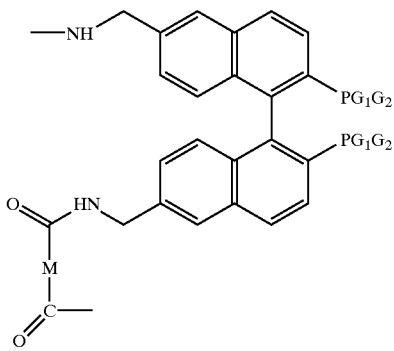

in which

G₁ and G₂ are as defined above and M is as defined for J. Preferred meanings of G₁, G₂ and J are as defined above.

The condensation of the diphosphine with the dicarboxylic acid or its activated derivative is generally carried out in a solvent.

When the dicarboxylic acid is used as such, it may be advantageous to carry out the condensation in the presence of a catalyst, for example a strong acid, such as hydrochloric acid or sulfuric acid, or else in the presence of a coupling agent, such as those commonly used in peptide synthesis.

Mention may be made, among known coupling agents, of N-hydroxylated derivatives, such as N-hydroxysuccinimide and 1-hydroxybenzotriazole; disulfides, such as 2,2'-dipyridyl disulfide; succinic acid derivatives, such as N,N'-disuccinimidyl carbonate; phosphinic chlorides, such as N,N'-bis(2-oxo-3-oxazolidinyl)phosphinic chloride; oxalates, such as N,N'-disuccinimidyl oxalate (DSO), N,N'-diphthalimide oxalate (DPO), N,N'-bis(norbornenylsuccinimidyl) oxalate (BNO), 1,1'-bis (benzotriazolyl) oxalate (BBTO), 1,1'-bis(6-chlorobenzotriazolyl) oxalate (BCTO) or 1,1'-bis(6-trifluoromethylbenzotriazolyl) oxalate (BTBO); triarylphosphines, such as triphenylphosphine; a combination of a di(lower alkyl) azodicarboxylate and a triarylphosphine, such as a combination of diethyl azodicarboxylate and triphenylphosphine; N-(lower alkyl)-5-arylisoxazolium-3'-sulfonates, such as N-ethyl-5-phenylisoxazolium-3'-sulfonate; carbodiimide derivatives, including N',N'-dicycloalkylcarbodiimides, such as N',N'-dicyclohexylcarbodiimide (DCC) or 1-ethyl-3-(3-dimethylaminopropyl)carbodiimide (EDAPC); diheteroaryl diselenides, such as di-2-pyridyl diselenide; arylsulfonyltriazolides, such as p-nitrobenzenesulfonyltriazolide; 2-halo-1-(lower alkyl) pyridinium halides, such as 2-chloro-1-methylpyridinium iodide; diarylphosphoryl azides, such as diphenylphosphoryl azide (DPPA); imidazole derivatives, such as 1,1'-oxalyldiimidazole or N,N'-carbonyldiimidazole; benzotriazole derivatives, such as 1-hydroxybenzotriazole (HOBT); and dicarboximide derivatives, such as N-hydroxy-5-norbornene-2,3-dicarboximide (HONB). Preference is given, among these, to carbodiimide derivatives.

The reaction can take place within a wide temperature range.

Depending upon the reactivity of the reactants brought together, the reaction temperature oscillates between –20° C. and 100° C.

When the polymerization involves the reaction of an activated derivative of the dicarboxylic acid with a diphosphine, a relatively low temperature, preferably of between 0° C. and 40° C., is sufficient.

Conversely, when the dicarboxylic acid as such is involved in the reaction, the temperature is preferably between 50 and 80° C.

The concentration of the reactants in the reaction medium is not determining according to the invention. It can vary between 0.05 and 1 mol/l.

The molar ratio of the dicarboxylic acid or its activated derivative to the diphosphine generally varies between 0.8 and 1.5, preferably between 0.9 and 1.2.

A typical procedure, illustrating the preparation of a polyamide starting from a carboxylic acid chloride, is as follows. 3.75 mmol of the carboxylic acid chloride are added to a solution of 4.16 mmol of diphosphine in 5 ml of N,N-dimethylacetamide. The reaction mixture is kept stirred overnight at ambient temperature (18 to 30° C.). The polyamide is then precipitated from 150 ml of distilled water. The polymer is filtered off on a sintered glass funnel and washed with water and then with isopropanol.

The general conditions for carrying out the polymerization and isolation of the polymer will be easily determined by a person skilled in the art, it being understood that the preferred polyamides of the invention exhibit a degree of polymerization of between 2 and 100, for example between 5 and 100, preferably between 2 and 50, better still between 4 and 25.

A person skilled in the art will choose the degree of polymerization so that the resulting polymer is insoluble in the solvent or mixtures of solvents used in the asymmetric reaction which has to be catalyzed.

When the polymer is a polythiourea, the latter can be prepared by condensation of a chiral diphosphine carrying two amino or aminomethyl functional groups with one or more diisothiocyanates.

Use will preferably be made of a diisothiocyanate exhibiting a $C_2$ axis of symmetry, such as, for example:

1,4-butane diisothiocyanate;
1,3-propane diisothiocyanate;
bis(4-isothiocyanatophenyl)sulfone; or
1,4-phenylene diisothiocyanate.

More generally, the diisothiocyanate corresponds to the formula:

$$S=C=N-J-N=C=S$$

in which J is as defined above.

For the implementation of the condensation, a person skilled in the art may draw inspiration from the reaction conditions described above for the preparation of the polyureas.

When the polymer is a polyimide, the latter can be prepared by condensation of a chiral diphosphine carrying two amino or aminomethyl functional groups with one or more tetracarboxylic acids or tetracarboxylic acid dianhydrides.

For the preparation of these polyimides, a person skilled in the art may draw inspiration from D. C. Sherrington, Chem. Commun., 1998, 2275–2286.

The polyimides are advantageously prepared in two stages. In a first stage, a polyamide is formed. This stage is carried out, for example, at a temperature of between 15 and 50° C., preferably of between 20 and 30° C., in a polar aprotic solvent (such as an amide of the following types: formamide, dimethylacetamide or N-methyl-2-pyrrolidinone, preferably dimethylacetamide). In a second stage, the polyimide is formed. This second stage can be carried out by treatment with a mixture of acetic anhydride and pyridine at a temperature of between –100° C. and 10° C., preferably of between –78 and –50° C.

According to one of its aspects, the invention thus relates to a process for the preparation of a polymer of the invention comprising the polymerization of a chiral diphosphine exhibiting a $C_2$ axis of symmetry, with the exclusion of any other element of symmetry, with one or more polymerizable monomers, said chiral phosphine being composed of a chiral body carrying two identical functional groups capable of reacting with said polymerizable monomers.

The invention also relates to the racemic polymer corresponding to the optically active polymer of the invention.

This polymer can be prepared simply by polymerization of the appropriate diphosphine with one or more polymerizable monomers, said diphosphine carrying two identical functional groups capable of reacting with said polymerizable monomers.

The diphosphines used in this reaction are preferably the racemic diphosphines corresponding to the preferred chiral diphosphines defined above. Thus, according to a preferred embodiment of the invention, the racemic diphosphine is composed of a racemic basic backbone of formula I.1, I.2, I.3, I.4, I.5, I.6 or I.7 carrying two identical functional groups.

Likewise, the polymerizable monomers preferably used for this polymerization are those described above for the preparation of the optically active polymers.

The operating conditions for this polymerization will be easily determined by a person skilled in the art by analogy with those provided for the polymerization reaction resulting in the optically active polymer.

The polymers of the invention can be used as ligands for the preparation of metal complexes intended for the asymmetric catalysis of numerous reactions, such as reactions for the hydrogenation, hydrosilylation or hydroboration of unsaturated compounds, for the epoxidation of allyl alcohols, for the vicinal hydroxylation, hydrovinylation, hydroformylation, cyclopropanation, carbonylation or isomerization of olefins, for the polymerization of propylene, for the addition of organometallic compounds to aldehydes or for allylic alkylation, reactions of aldol type and Diels-Alder reactions.

Such complexes are in particular rhodium, iridium, ruthenium, palladium, platinum, cobalt and nickel complexes.

Preference is in particular given, among the preceding complexes, to rhodium, ruthenium, iridium, platinum and palladium complexes. In the context of the invention, ruthenium, rhodium and iridium complexes are the most advantageous.

Specific examples of said complexes of the present invention are given below, without a limiting nature.

In the following formulae, $P_p$ is the polymer.

A preferred group of rhodium and iridium complexes is defined by the formula:

$$[\text{MeLig}_2P_p]Y_1 \qquad \qquad \text{XI}$$

in which $P_p$ is the polymer;
$Y_1$ is a coordinating anionic ligand;
Me is rhodium or iridium;
Lig is a neutral ligand.

Among these compounds, those in which:

Lig is an olefin having from 2 to 12 carbon atoms;
$Y_1$ is a $PF_6^-$, $PCl_6^-$, $BF_4^-$, $BCl_4^-$, $SbF_6^-$, $SbCl_6^-$, $BPh_4^-$, $ClO_4^-$, $CN^-$, $CF_3SO_3^-$ or halogen, preferably $Cl^-$ or $Br^-$, anion, a 1,3-diketonate anion, an alkylcarboxylate anion or a haloalkylcarboxylate anion with a lower alkyl (preferably $C_1$–$C_6$) radical and/or halogen atoms, are particularly preferred.

In the formula XI, $Lig_2$ can be two Lig ligands as defined above or a bidentate ligand, such as a polyunsaturated and linear or cyclic bidentate ligand comprising at least two unsaturations.

It is preferable, according to the invention, for $Lig_2$ to be 1,5-cyclooctadiene or norbornadiene or else for Lig to be ethylene.

The term "lower alkyl radicals" is understood to mean generally a linear or branched alkyl radical having from 1 to 4 carbon atoms.

Other iridium complexes are those of formula:

$$[\text{IrLig}P_p]Y_1 \qquad \qquad \text{XII}$$

in which Lig, $P_p$ and $Y_1$ are as defined for the formula XI.

A preferred group of ruthenium complexes is composed of the compounds of formula:

$$[\text{Ru}Y_1^1Y_1^2P_p] \qquad \qquad \text{XIII}$$

in which:

$P_p$ is the polymer of the invention;
$Y_1^1$ and $Y_1^2$, which are identical or different, are a $PF_6^-$, $PCl_6^-$, $BF_4^-$, $BCl_4^-$, $SbF_6^-$, $SbCl_6^-$, $BPh_4^-$, $ClO_4^-$ or $CF_3SO_3^-$ anion, a halogen atom, more particularly a chlorine or bromine atom, or a carboxylate anion, preferably an acetate or trifluoroacetate anion.

Other ruthenium complexes are those corresponding to the following formula XIV:

$$[RuY_1^3 ar P_p Y_1^4] \quad \text{XIV}$$

in which
- $P_p$ is the polymer of the invention;
- ar is benzene, p-methylisopropylbenzene or hexamethylbenzene;
- $Y_1^3$ is a halogen atom, preferably a chlorine or bromine atom;
- $Y_1^4$ is an anion, preferably a $PF_6^-$, $PCl_6^-$, $BF_4^-$, $BCl_4^-$, $SbF_6^-$, $SbCl_6^-$, $BPh_4^-$, $ClO_4^-$ or $CF_3SO_3^-$ anion.

It is also possible to employ, in the process of the invention, complexes based on palladium and platinum.

Mention may be made, as more specific examples of said complexes, of, inter alia, $Pd(hal)_2 P_p$ and $Pt(hal)_2 P_p$, where $P_p$ is the polymer of the invention and hal is halogen, such as, for example, chlorine.

The complexes comprising the polymer of the invention as ligand and the transition metal can be prepared according to known processes described in the literature.

The complexes are generally prepared from a precatalyst, the nature of which varies according to the transition metal selected.

In the case of rhodium complexes, the precatalyst is, for example, one of the following compounds: $[Rh^1(CO)_2Cl]_2$; $[Rh^1(COD)Cl]_2$, where COD denotes cyclooctadiene; or $Rh^1(acac)(CO)_2$, where acac denotes acetylacetonate.

In the case of ruthenium complexes, precatalysts which are particularly well suited are bis(2-methylallyl)(cycloocta-1,5-diene)ruthenium and $[RuCl_2(benzene)]_2$. Mention may also be made of $Ru(COD)(\eta^3-(CH_2)_2CHCH_3)_2$.

By way of example, starting from bis(2-methylallyl)(cycloocta-1,5-diene)ruthenium, a solution or suspension is prepared comprising the metal precatalyst, the polymer of the invention and a completely degassed solvent, such as acetone (the concentration of polymer in the solution or suspension varying between 0.001 and 1 mol/l), to which is added a methanolic hydrobromic acid solution. The ratio of the ruthenium to the bromine advantageously varies between 1:1 and 1:4, preferably between 1:2 and 1:3. The molar ratio of the ligand to the transition metal is, for its part, approximately 1. It can be between 0.8 and 1.2.

When the precatalyst is $[RuCl_2(benzene)]_2$, the complex is prepared by mixing the precatalyst, the polymer ligand and an organic solvent and is optionally maintained at a temperature of between 15 and 150° C. for 1 minute to 24 hours, preferably 30 to 120° C. for 10 minutes to 5 hours.

Mention may be made, as solvent, of aromatic hydrocarbons (such as benzene, toluene and xylene), amides (such as formamide, dimethylformamide, dimethylacetamide, N-methyl-2-pyrrolidinone or hexamethylphosphoramide, alcohols (such as ethanol, methanol, n-propanol and isopropanol) and their mixtures.

Preferably, when the solvent is an amide, in particular dimethylformamide, the mixture of the polymer, precatalyst and solvent is heated between 80 and 120° C.

In an alternative form, when the solvent is a mixture of an aromatic hydrocarbon (such as benzene) with an alcohol (such as ethanol), the reaction medium is heated at a temperature of between 30 and 70° C.

The catalyst is then recovered according to conventional techniques (filtration or crystallization) and used in asymmetric reactions. Nevertheless, the reaction which has to be catalyzed by the complex thus prepared can be carried out without intermediate isolation of the catalyst complex.

The case of hydrogenation is set out in detail subsequently.

The unsaturated substrate, in solution in a solvent comprising the catalyst, is placed under hydrogen pressure, The hydrogenation is carried out, for example, at a pressure varying between 1.5 and 100 bar and at a temperature of between 20° C. and 100° C.

The exact processing conditions depending on the nature of the substrate which has to be hydrogenated. Nevertheless, in the general case, a pressure of 20 to 80 bar, preferably of 40 to 60 bar, and a temperature of 30 to 70° C. are particularly well suited.

The reaction medium can be composed of the reaction medium in which the catalyst was obtained. The hydrogenation reaction then takes place in situ.

In an alternative form, the catalyst is isolated from the reaction medium in which it was obtained. In this case, the reaction medium of the hydrogenation reaction is composed of one or more solvents selected in particular from aliphatic $C_1-C_5$ alcohols, such as methanol or propanol, and an amide as defined above, preferably dimethylformamide, optionally as a mixture with benzene.

When the hydrogenation reaction takes place in situ, it is desirable to add, to the reaction medium, one or more solvents selected from those mentioned above and more particularly one or more aliphatic alcohols.

According to a preferred embodiment, completely degassed methanol and the substrate are added to the reaction medium comprising the complex. The amount of methanol or more generally of solvent which can be added is such that the concentration of the substrate in the hydrogenation reaction medium is between $1 \times 10^{-3}$ and 10 mol/l, preferably between 0.01 and 1 mol/l.

The molar ratio of the substrate to the catalyst generally varies from 1/100 to 1/100000, preferably from 1/20 to 1/2000. This ratio is, for example, 1/1000.

The rhodium complexes prepared from the polymer ligands of the invention are more especially appropriate for the asymmetric catalysis of reactions for the isomerization of olefins.

The ruthenium complexes prepared from the polymer ligands of the invention are more especially appropriate for the asymmetric catalysis of reactions for the hydrogenation of carbonyl bonds, of C=C bonds and of C=N bonds.

As regards the hydrogenation of double bonds, the appropriate substrates are of α,β-unsaturated carboxylic acid and/or derivatives of α,β-unsaturated carboxylic acid type. These substrates are disclosed in EP 95943260.0.

The α,β-unsaturated carboxylic acid or its derivative corresponds more particularly to the formula A:

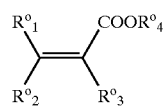

(A)

in which
- $R^o_1$, $R^o_2$, $R^o_3$ and $R^o_4$ are a hydrogen atom or any hydrocarbonaceous group, in so far as:
  - if $R^o_1$ is different from $R^o_2$ and other than a hydrogen atom, then $R^o_3$ can be any hydrocarbonaceous or functional group denoted by R,
  - if $R^o_1$ or $R^o_2$ is a hydrogen atom and if $R^o_1$ is different from $R^o_2$, then $R^o_3$ is other than a hydrogen atom and different from $-COOR^o_4$,
  - if $R^o_1$ is identical to $R^o_2$ and is any hydrocarbonaceous or functional group denoted by R, then $R^o_3$ is different from $-CH-(R)_2$ and different from $-COOR^o_4$, it being possible for one of the $R°_1$, $R°_2$ and $R°_3$ groups to be a functional group.

Mention may be made, as specific example, of, inter alia, 2-methyl-2-butenoic acid.

A first group of preferred substrates is formed by substituted acrylic acids which are precursors of amino acids and/or derivatives.

The term "substituted acrylic acids" is understood to mean all the compounds with a formula derived from that of acrylic acid by substitution of at most two of the hydrogen atoms carried by the ethylenic carbon atoms by a hydrocarbonaceous group or by a functional group.

They can be symbolized by the following chemical formula:

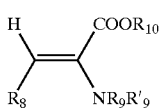

(A1)

in which:

$R_9$ and $R'_9$, which are identical or different, are a hydrogen atom, a linear or branched alkyl group having from 1 to 12 carbon atoms, a phenyl group or an acyl group having from 2 to 12 carbon atoms, preferably an acetyl or benzoyl group, $R_8$ is a hydrogen atom, an alkyl group having from 1 to 12 carbon atoms, a cycloalkyl radical having from 3 to 8 carbon atoms, an arylalkyl radical having from 6 to 12 carbon atoms, an aryl radical having from 6 to 12 carbon atoms or a heterocyclic radical having from 4 to 7 carbon atoms, $R_{10}$ is a hydrogen atom or a linear or branched alkyl group having from 1 to 4 carbon atoms.

Mention may more particularly be made of:

methyl α-acetamidocinnamate, methyl acetamidoacrylate, benzamidocinnamic acid,

α-acetamidocinnamic acid.

A second preferred group of substrates is composed of itaconic acid and its derivatives of formula:

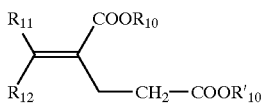

A2 in which:

$R_{11}$ and $R_{12}$, which are identical or different, are a hydrogen atom, a linear or branched alkyl group having from 1 to 12 carbon atoms, a cycloalkyl radical having from 3 to 8 carbon atoms, an arylalkyl radical having from 6 to 12 carbon atoms, an aryl radical having from 6 to 12 carbon atoms or a heterocyclic radical having from 4 to 7 carbon atoms, $R_{10}$ and $R'_{10}$, which are identical or different, are a hydrogen atom or a linear or branched alkyl group having from 1 to 4 carbon atoms.

Mention may in particular be made, as more specific examples, of itaconic acid and dimethyl itaconate.

A third preferred group of substrates is defined by the formula A3:

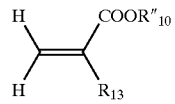

A3 in which $R''_{10}$ is a hydrogen atom or a linear or branched alkyl group having from 1 to 4 carbon atoms, $R_{13}$ is a phenyl or naphthyl group, optionally carrying one or more substituents.

Mention may be made, as specific examples, of the substrates resulting by hydrogenation in 2-(3-benzoylphenyl)propionic acid (Ketoprofen®), 2-(4-isobutylphenyl)propionic acid (Ibuprofen®) or 2-(5-methoxynaphthyl)propionic acid (Naproxen®).

As regards the hydrogenation of carbonyl bonds, the appropriate substrates of ketone type correspond more preferably to the formula B:

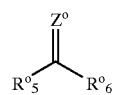

B in which:

$R°_5$ is different from $R°_6$ $R°_5$ and $R°_6$ are a hydrocarbonaceous radical having from 1 to 30 carbon atoms optionally comprising one or more functional groups, $R°_5$ and $R°_6$ can form a ring optionally comprising another heteroatom, $Z°$ is or comprises an oxygen or nitrogen heteroatom or a functional group comprising at least one of these heteroatoms.

These compounds are clearly disclosed in FR 9608060 and EP 97930607.3.

A first preferred group of such ketone substrates has for formula B1:

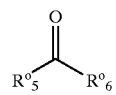

B1 in which:

$R°_5$ is different from $R°_6$ and the $R°_5$ and $R°_6$ radicals are a hydrocarbonaceous radical having from 1 to 30 carbon atoms optionally comprising another ketone and/or acid, ester, thioacid or thioester functional group;

$R°_5$ and $R°_6$ can form a substituted or unsubstituted carbocyclic or heterocyclic ring having from 5 to 6 atoms.

Preference is very particularly given, among these compounds, to the ketones selected from:

methyl phenyl ketone,
isopropyl phenyl ketone,
cyclopropyl phenyl ketone,
allyl phenyl ketone, p-methylphenyl methyl ketone,
benzyl phenyl ketone,
phenyl triphenylmethyl ketone,
o-bromoacetophenone,
α-bromoacetone
α-dibromoacetone,
α-chloroacetone,
α-dichloroacetone,
α-trichloroacetone,
1-chloro-3,3-dichloroacetone
1-chloro-2-oxobutane,
1-fluoro-2-oxobutane,
1-chloro-3-methyl-2-butanone,
α-chloroacetophenone,
1-chloro-3-phenylacetone,
α-methylaminoacetone,
α-dimethylaminoacetone,
1-butylamino-2-oxopropane,
1-dibutylamino-2-oxopropane,
1-methylamino-2-oxobutane,
1-dimethylamino-2-oxobutane,
1-dimethylamino-3-methyl-2-oxobutane,
1-dimethylamino-2-oxopentane,
α-dimethylaminoacetophenone,
α-hydroxyacetone,
1-hydroxy-3-methyl-2-butanone,
1-hydroxy-2-oxobutane,
1-hydroxy-2-oxopentane,
1-hydroxy-2-oxohexane,
1-hydroxy-2-oxo-3-methylbutane,
α-hydroxyacetophenone,
1-hydroxy-3-phenylacetone,
α-methoxyacetone,
α-methoxyacetophenone,
α-ethoxyacetone,
α-butoxyacetophenone,
α-chloro-p-methoxyacetophenone,
α-naphthenone,
1-ethoxy-2-oxobutane,
1-butoxy-2-oxobutane,
α-dimethoxyphosphorylacetone,
3-oxotetrahydrothiophene.

The substrates of aldehyde/ketone type exhibiting a second carbonyl group in the α, β, γ or 67 position with respect to the first carbonyl group are also particularly appropriate in the context of the invention. Examples of such diketone compounds are:

α-formylacetone,
diacetyl,
3,4-dioxohexane,
4,5-dioxooctane,
1-phenyl-1,2-dioxopropane,
1-phenyl-2,3-dioxobutane,
diphenylglyoxal,
p-methoxydiphenylglyoxal,
1,2-cyclopentanedione,
1,2-cyclohexanedione,
acetylacetone,
3,5-heptanedione,
4,6-nonanedione,
5,7-undecadione,
2,4-hexanedione,
2,4-heptadione,
2,4-octanedione,
2,4-nonanedione,
3,5-nonanedione,
3,5-decanedione,
2,4-dodecanedione,
1-phenyl-1,3-butanedione,
1-phenyl-1,3-pentanedione,
1-phenyl-1,3-hexanedione,
1-phenyl-1,3-heptanedione,
3-methyl-2,4-pentanedione,
1,3-diphenyl-1,3-propanedione,
1,5-diphenyl-2,4-pentanedione,
1,3-di(trifluoromethyl)-1,3-propanedione,
3-chloro-2,4-pentanedione,
1,5-dichloro-2,4-pentanedione,
1,5-dihydroxy-2,4-pentanedione,
1,5-dibenzyloxy-2,4-pentanedione,
1,5-diamino-2,4-pentanedione,
1,5-di(methylamino)-2,4-pentanedione,
1,5-di(dimethylamino)-2,4-pentanedione,
methyl 3,5-dioxohexanoate,
3-methoxycarbonyl-2,4-pentanedione,
3-ethoxycarbonyl-2,4-pentanedione,
1,3-cyclopentanedione,
1,3-cyclohexanedione,
1,3-cycloheptanedione,
5-ethoxycarbonyl-1,3-cyclopentanedione,
2-acetyl-1-cyclopentanone,
2-acetyl-1-cyclohexanone.

Mention may be made, as other substrates which are particularly well suited, of keto acids or their derivatives and keto thioacids or their derivatives with a functional group (acid, ester, thioacid or thioester) in the a α, β, γ or δ position with respect to the carbonyl group. Examples thereof are:

2-acetylbenzoic acid,
pyruvic acid,
2-oxobutanoic acid,
3-methyl-2-oxobutanoic acid,
phenylglyoxylic acid,
phenylpyruvic acid,
p-methoxyphenylpyruvic acid,
3,4-dimethoxyphenylpyruvic acid,
methyl acetoacetate,
ethyl acetoacetate,
n-propyl acetoacetate,
isopropyl acetoacetate,
n-butyl acetoacetate,
t-butyl acetoacetate,
n-pentyl acetoacetate,
n-hexyl acetoacetate,
n-heptyl acetoacetate,
n-octyl acetoacetate,
methyl 3-oxopentanoate,
methyl 3-oxohexanoate,
methyl 3-oxoheptanoate,
ethyl 3-oxooctanoate,
ethyl 3-oxononanoate,
ethyl 3-oxodecanoate,
ethyl 3-oxoundecanoate,
ethyl 3-oxo-3-phenylpropanoate,
ethyl 4-phenyl-3-oxobutanoate,
methyl 5-phenyl-3-oxopentanoate,
ethyl 3-oxo-3-(p-methoxyphenyl)propanoate,
methyl 4-chloroacetoacetate,
methyl 4-chloroacetoacetate,
ethyl 4-fluoroacetoacetate,
ethyl 3-trifluoromethyl-3-oxopropanoate, ethyl 4-hydroxy-3-oxobutanoate,
methyl 4-methoxyacetoacetate,
methyl 4-tert-butoxyacetoacetate,
methyl 4-benzyloxy-3-oxobutanoate,
ethyl 4-benzyloxy-3-oxobutanoate,
methyl 4-amino-3-oxobutanoate,
ethyl 3-methylamino-3-oxobutanoate,
methyl 4-dimethylamino-3-oxobutanoate,
ethyl 4-dimethylamino-3-oxobutanoate,
methyl 2-methylacetoacetate,
ethyl 2-methylacetoacetate,
ethyl 2-chloroacetoacetate,
diethyl 2-acetylsuccinate,
diethyl 2-acetylglutarate,
dimethyl acetylmalonate,
thiomethyl acetoacetate,
thioethyl acetoacetate,
thiophenyl acetoacetate,
methyl pyruvate,
ethyl 3-methyl-2-oxobutanoate,
ethyl phenylglyoxolate,
methyl phenylpyruvate,
ethyl phenylpyruvate,
3-oxobutanoic dimethylamide,
3-oxobutanoic benzylamide,
2-(ethoxycarbonyl)cyclopentanone,
2-(ethoxycarbonyl)cyclohexanone,
ketopentalactone,
4-oxopentanoic acid,
4-oxohexanoic acid,
4-oxoheptanoic acid,
4-oxodecanoic acid,
4-oxododecanoic acid,
4-phenyl-4-oxybutyric acid,
4-(p-methoxyphenyl)-4-oxybutyric acid,
4-(3,4-dimethoxyphenyl)-4-oxobutyric acid,
4-(3,4,5-trimethoxyphenyl)-4-oxobutyric acid,
4-(p-chlorophenyl)-4-oxybutyric acid,
4-phenyl-4-oxobutyric acid.

It should be noted that, when the asymmetric hydrogenation of a γ-keto acid or derivative has to be carried out, the product obtained is generally a γ-butyrolactone derivative and, in the case of a δ-keto acid, it is a valerolactone derivative.

Mention may be made, as other examples of ketones, of, inter alia, the following monocyclic or polycyclic, saturated or unsaturated, cyclic ketone compounds:

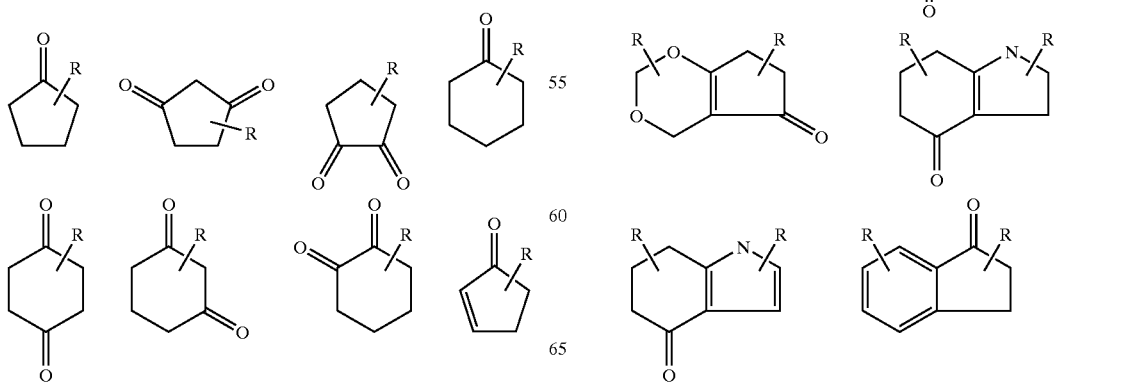

-continued

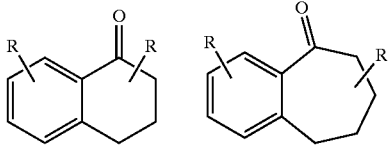

where R is a phenyl which is or is not substituted by alkyl or alkoxy radicals or a halogen atom; or R is an alkyl or cycloalkyl group which is or is not substituted by alkyl or alkoxy radicals or a halogen atom or a hydroxyl, ether or amine group; or R is a halogen atom or a hydroxyl, ether or amine group.

It is also possible to employ ketones of steroid type (for example, 3-cholestanone or 5-cholesten-3-one).

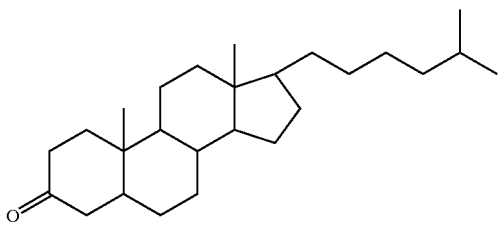

Mention may be made, as other ketone substrates, of the compounds of formula B2:

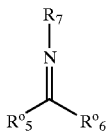

B2 in which:
  $R°_5$, which is different from $R°_6$, has the meaning given above,
  $R_7$ is:
    a hydrogen atom,
    a hydroxyl group,
    an $OR_{17}$ group,
    an $R_{17}$ hydrocarbonaceous radical,
    a group of formula

a group of formula

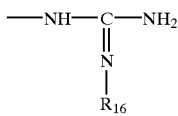

with $R_{14}$, $R_{15}$, $R_{16}$ and $R_{17}$, which are a hydrogen atom or a hydrocarbonaceous group having from 1 to 30 carbon atoms.

Examples of compounds of formula B2 are:
N-alkylketoimine, such as:
  N-isobutyl-2-iminopropane
  N-isobutyl-1-methoxy-2-iminopropane N-arylalkylketoimine, such as:
  N-benzyl-1-imino-1-(phenyl)ethane
  N-benzyl-1-imino-1-(4-methoxyphenyl)ethane
  N-benzyl-1-imino-1-(2-methoxyphenyl)ethane
N-arylketoimine, such as:
  N-phenyl-2-iminopentane
  N-(2,6-dimethylphenyl)-2-iminopentane
  N-(2,4,6-trimethylphenyl)-2-iminopentane
  N-phenyl-1-imino-1-phenylethane
  N-phenyl-1-methoxy-2-iminopropane
  N-(2,6-dimethylphenyl)-1-methoxy-2-iminopropane
  N-(2-methyl-6-ethylphenyl)-1-methoxy-2-iminopropane
compounds of the following type: optionally N-acylated or N-benzoylated hydrazone:
  1-cyclohexyl-1-(2-benzoylhydrazono)ethane,
  1-phenyl-1-(2-benzoylhydrazono)ethane,
  1-(p-methoxyphenyl)-1-(2-benzoylhydrazono)ethane,
  1-(p-ethoxyphenyl)-1-(2-benzoylhydrazono)ethane,
  1-(p-nitrophenyl)-1-(2-benzoylhydrazono)ethane,
  1-(p-bromophenyl)-1-(2-benzoylhydrazono)ethane,
  1-(p-ethoxycarbonylphenyl)-1-(2-benzoylhydrazono)ethane,
  1,2-diphenyl-1-(2-benzoylhydrazono)ethane,
  3-methyl-2-(2-(p-dimethylaminobenzoyl)hydrazono)butane,
  1-phenyl-1-(2-(p-methoxybenzoyl)hydrazono)ethane,
  1-phenyl-1-(2-(p-dimethylaminobenzoyl)hydrazono)ethane,
  ethyl 2-(2-benzoylhydrazono)propionate
  methyl 2-(2-benzoylhydrazono)butyrate
  methyl 2-(2-benzoylhydrazono)valerate
  methyl 2-phenyl-2-(2-benzoylhydrazono)acetate.

Other starting substrates are semicarbazones and cyclic ketoimines with an endo- or exocyclic bond, such as:

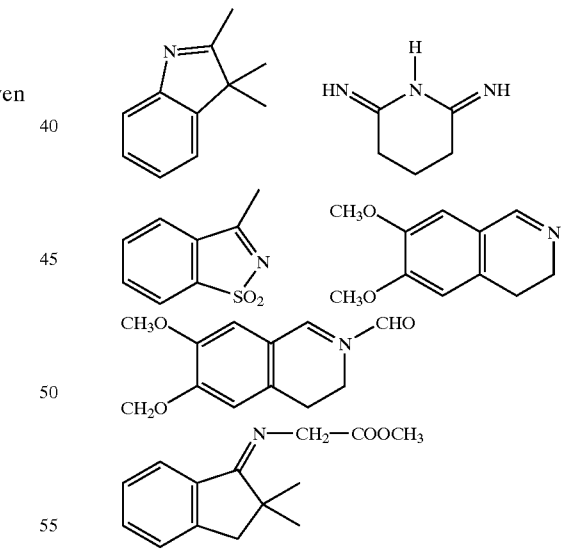

According to a preferred embodiment of the invention, the substrate is an aromatic ketone (phenyl methyl ketone, naphthyl methyl ketone, p-methoxyphenyl methyl ketone, p-trifluoromethylphenyl methyl ketone and o-methylphenyl methyl ketone), an α-keto ester (such as methyl benzoylformate and methyl pyruvate), a β-keto ester (such as methyl acetoacetate and methyl 3-oxovalerate), an α,β-ethylenic ester (such as an ester of tiglic acid and of itaconic acid) or an unsaturated amino acid or one of its derivatives (such as methyl 2-acetamidoacrylate).

Thus, according to another of its aspects, the invention relates to the use of a polymer of the invention for the preparation of a metal complex intended for asymmetric catalysis and more specifically of a ruthenium, iridium or rhodium complex.

According to a preferred embodiment of the invention, the metal complexes are intended for the asymmetric catalysis of reactions for the hydrogenation of C=O bonds and of C=C bonds.

Furthermore, the invention relates to the use of the combination of an optically active polymer according to the invention with a diamine, which may or may not be chiral, for the selective reduction of ketones.

The diamines which can be used for this purpose are the optically active diamines disclosed in WO 97/20789 and the corresponding racemic diamines.

According to a particularly preferred embodiment of the invention, the diamine is 1,2-diamino-1,2-diphenylethane; 1,1-bis(p-methoxyphenyl)-2-methyl-1,2-diaminoethane; 1,1-bis(p-methoxyphenyl)-2-isobutyl-1,2-diaminoethane; or 1,1-bis(p-methoxyphenyl)-2-isopropyl-1,2-diaminoethane.

Examples of chiral diamines are more particularly those of formula:

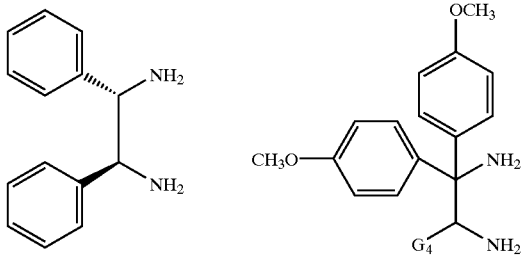

in which $G_4$ is alkyl, for example methyl, isobutyl or isopropyl.

The ketones which can be reduced according to this process are those described above.

The conditions for carrying out the reduction are those generally described above.

In addition, the invention relates to the use of the combination of a racemic polymer according to the invention with a chiral diamine for the selective reduction of ketones.

The chiral diamine which can be used is as disclosed in WO 97/20789, the ketones and the operating conditions being as defined above.

Preparation 1
Preparation of (S)-6,6'-dibromo-2,2'-dihydroxy-1,1'-binaphthyl 7.7 g (26.9 mol) of (S)-2,2'-dihydroxy-1,1'-binaphthyl are dissolved in 145 ml of dichloromethane. The solution is cooled to −75° C. and then 3.66 ml of $Br_2$ (71.7 mmol) are added dropwise over 30 minutes while constantly stirring. The solution is stirred for a further 2 and a half hours before being brought back to ambient temperature. After addition of 180 ml of sodium bisulfite (10% by mass), the organic phase is washed with a saturated NaCl solution and dried over $Na_2SO_4$. After evaporating the solvent, the solid obtained is recrystallized from a toluene/cyclohexane mixture at 80° C. to give 9.8 g (22 mmol, 82% yield) of the expected product.

The optical rotation, as measured on a Perkin-Elmer 241 polarimeter (1=10 cm, 25° C., concentration c in g/dm$^3$), is 124.3 at c=1.015 and 578 nm.

For the preparation of the title dibrominated derivative, reference may be made to G. Dotsevi et al., J. Am. Chem. Soc., 1979, 101, 3035.

Preparation 2
Preparation of (S)-6,6'-dibromo-2,2'-bis (trifluoromethanesulfonyloxy)-1,1'-binaphthyl 9.52 g (21.4 mmol) of (S)-6,6'-dibromo-2,2'-dihydroxy-1,1'-binaphthyl are dissolved in a mixture of 40 ml of $CH_2Cl_2$ and 5.4 ml of pyridine. After having cooled the mixture to 0° C., 8.7 ml (14.5 g, 51.5 mmol) of triflic anhydride (($CF_3SO_2)_2O$) are slowly added. After stirring for 6 h, the solvent is evaporated and the reaction mass is dissolved in 100 ml of ethyl acetate. After having washed with a 5% aqueous HCl solution, a saturated $NaHCO_3$ solution and a saturated NaCl solution, the organic phase is dried over $Na_2SO_4$ and then the solvent is evaporated under reduced pressure. The yellow oil is purified by chromatography on silica ($CH_2Cl_2$) to give 12.5 g (17.7 mmol, 83% yield) of the expected product.

$[\alpha]_D$=151.3 (c=1.005, THF), the optical rotation being measured under the same conditions as in preparation 1 but at the wavelength corresponding to the D line of sodium.

Reference may also made, for the preparation of the title compound, to the studies by M. Vondenhof, Tetrahedron Letters, 1990, 31, 985.

Preparation 3
Preparation of (S)-6,6'-dibromo-2,2'-bis (trifluoromethanesulfonyloxy)-1,1'-binaphthyl In an alternative form, the title compound can be prepared from (R)-6,6'-dibromo-2,2'-dihydroxy-1,1'-binaphthyl by following the procedure described below.

10.0 g (22.52 mmol) of (R)-6,6'-dibromo-2,2'-dihydroxy-1,1'-binaphthyl are dissolved in a solution of 6.3 g (0.11 mol) of KOH in 300 ml of degassed water. The mixture is cooled to 0° C. and subsequently a solution of 11.4 ml (19.1 g, 68 mmol) of triflic anhydride in 200 ml of $CCl_4$ is added over 45 minutes so that the temperature does not exceed 10° C. After having stirred for 30 min, 300 ml of $CH_2Cl_2$ are added. The organic phase is washed with water and then dried over $MgSO_4$. 15.89 g of crude product are subsequently purified by chromatography on silica (1/1 $CH_2Cl_2$/cyclohexane) to give 12.94 g (18.27 mmol, 81% yield) of pure product.

$[\alpha]_D$=−153.2° (c=0.945, THF), the optical rotation being measured under the same conditions as in preparation 1 but at the wavelength corresponding to the D line of sodium.

$^1$H NMR (CDCl$_3$, 200 MHz): δ (ppm): 7.07 (d ($J_{H-H}$=7.07), CH, 2H), 7.48 (dd ($J^1_{H-H}$=9.05, $J^2_{H-H}$=1.94), CH, 2H), 7.62 (d ($J_{H-H}$=9.11), CH, 2H), 8.06 (d, ($J_{H-H}$=9.13), CH, 2H), 8.18 (d ($J_{H-H}$=1.90), CH, 2H).

$^{13}$C NMR (CDCl$_3$, 200 MHz): δ (ppm)=118.1 (Cq ($J_{C-F}$=320)), 120.2 (Cq), 120.7 (CH), 122.0 (Cq), 123.4 (Cq), 128.2 (CH), 130.5 (CH), 131.4 (CH), 131.6 (Cq), 131.7 (CH), 133.4 (Cq).

Preparation 4
Preparation of (S)-6,6'-dicyano-2,2'-bis (trifluoromethanesulfonyloxy)-1,1'-binaphthyl 12.5 g (17.7 mmol) of the compound prepared in preparation 2 and 3.5 g (38.8 mmol) of CuCN are stirred at 180° C. in 20 ml of N-methylpyrrolidone for 4 h. After having cooled to ambient temperature, the black suspension is poured into a solution of 15 ml of diaminoethane in 35 ml of water. The solution is extracted several times with 30 ml of $CH_2Cl_2$ and the organic phase is washed with a 10% aqueous KCN solution and a saturated NaCl solution. After drying over $Na_2SO_4$, the solvent is evaporated under reduced pressure. The black oil thus obtained is purified by chromatography on silica (9/1 $CH_2Cl_2$/cyclohexane) to give 6.5 g (10.8 mmol, 61% yield) of pure product.

$[\delta]_D$=171.7 (c=1.15, THF), the optical rotation being measured under the same conditions as in preparation 1 but at the wavelength corresponding to the D line of sodium.

$^1$H NMR (CDCl$_3$, 200 MHz): δ (ppm): 7.30 (d (J$_{H-H}$=9.81), CH, 2H), 7.59 (dd (J$^1_{H-H}$=8.82, J$^2_{H-H}$=1.65), CH, 2H), 7.78 (d (J$_{H-H}$=9.11), CH, 2H), 8.29 (d (J$_{H-H}$=8.09), CH, 2H), 8.46 (d (J$_{H-H}$=1.29), CH, 2H).

$^{13}$C NMR (CDCl$_3$, 200 MHz): δ (ppm)=111.7 (CN), 118.0 (Cq), 118.1 (Cq (J$_{C-F}$=320)), 121.6 (Cq), 123.3 (Cq), 127.7 (CH), 128.9 (CH), 131.4 (Cq), 133.2 (CH), 134.4 (Cq), 134.5 (CH), 147.4 (Cq).

A person skilled in the art may refer, for the preparation of the title compound, to the studies by Friedman et al., J. Org. Chem., 1961, 26, 2522, and M. S. Neuman et al., J. Org, Chem., 1961, 26, 2525.

Preparation 5
Preparation of (S)-6,6'-dicyano-2,2'-bis(diphenylphosphino)-1,1'-binaphthyl A solution of NiCl$_2$dppe (371 mg, 0.7 mmol) and diphenylphosphine (3 ml, 17 mmol) in 14 ml of DMF (anhydrous and degassed) is heated for 30 minutes at 100° C. in a 100 ml three-necked round-bottomed flask surmounted by an argon inlet. (S)-6,6'-Dicyano-2,2'-bis(trifluoromethanesulfonyloxy)-1,1'-binaphthyl (4.4 g, 7.4 mmol) and DABCO (3.375 g, 30 mmol), dissolved in 20 ml of DMF, are added dropwise. The reaction medium is left at 100° C. After 1, 3 and 7 hours, 0.75 ml of diphenylphosphine is added. The solution is left to stir for 2 days. It is subsequently cooled to 0° C., then filtered under argon and washed with methanol (2×10 ml). The solid is finally dried under vacuum to provide the expected product with a yield of 50%.

Elemental analysis for C$_{46}$H$_{30}$N$_2$P$_2$
Calculated: C, 80.88; H, 4.43; N, 4.10; P, 9.07. Found: C, 81.61; H, 4.45; N, 4.11; P, 8.99.

$^1$H NMR (CDCl$_3$, 200 MHz) δ (ppm): 6.59 (d, 2H, CH), 6.87 (dd, 2H, CH), 6.92–6.99 (m, 4H, CH), 7.09 (t, 4H, CH), 7.17–7.31 (m, 12H, CH), 7.57 (d, 2H, CH), 7.95 (d, 2H, CH), 8.20 (s, 2H, CH).

$^{13}$C NMR (CDCl$_3$, 50 MHz) δ (ppm): 109.8 (CN), 119.0 (Cq), 126.3 (CH), 127.7 (CH), 128.4 (CH), 128.5 (CH), 128.5 (CH), 128.6 (CH), 128.8 (CH), 129.3 (CH), 132.0 (CH), 132.1 (Cq), 132.9 (CH (triplet J$_{C-P}$=11.7), 133.9 (Cq), 134.1 (Cq), 134.9 (CH (triplet J$_{C-P}$=9.9)), 136.8 (Cq), 140.6 (Cq).

$^{31}$P NMR (CDCl$_3$, 81 MHz) δ (ppm): −12.75.

Preparation 6
Preparation of (S)-6,6'-bis(aminomethyl)-2,2'-bis(diphenylphosphino)-1,1'-binaphthyl 557 mg (14.7 mmol) of LiAlH$_4$ are dissolved in a mixture of THF (30 ml)/toluene (60 ml) in a 250 ml round-bottomed flask placed under an argon atmosphere. (S)-6,6'-Dicyano-2,2'-bis(diphenylphosphino)-1,1'-binaphthyl (650 mg, 0.97 mmol) is added to this solution, which is stirred and brought to reflux for 4 hours. It is subsequently cooled to 0° C. 600 µl of water and 600 µl of 15% NaOH are added. 2 g of celite are then added and the mixture is filtered through a millipore filter under argon. 60 ml of dichloromethane are added and the mixture is stirred and again filtered. This operation is carried out three times. The organic phase obtained is washed with a saturated aqueous NaCl solution and then dried over Na$_2$SO$_4$. The solvent is evaporated to produce a yellow solid (657 mg, quantitative yield), characterized by NMR (proton, carbon and phosphorus), corresponding to the expected structure.

Elemental analysis for C$_{46}$H$_{38}$N$_2$P$_2$
Calculated: C, 80.59; H, 6.00; N, 3.55; P, 7.84; Found: C, 81.14; H, 5.51; N, 3.13; P, 7.90.

$^1$H NMR (CDCl$_3$, 200 MHz) δ (ppm): 1.68 (s, 4H, NH$_2$), 3.81 (s, 4H, CH$_2$), 6.72 (s, 4H, CH), 6.9–7.3 (m, 20H, CH), 7.33 (d, 2H, CH), 7.64 (s, 2H, CH), 7.76 (d, 2H, CH).

$^{31}$P NMR (CDCl$_3$, 81 MHz) δ (ppm): −15.08.

EXAMPLE 1
Preparation of a Polyurea Starting from (S)-6,6'-bis(aminomethyl)-2,2'-bis(diphenylphosphino)-1,1'-binaphthyl a) Polyurea 1

(S)-6,6'-Bis(aminomethyl)-2,2'-bis(diphenylphosphino)-1,1'-binaphthyl (200 mg, 0.29 mmol) is dissolved in 2 ml of degassed dichloromethane in a 10 ml round-bottomed flask and 2,6-diisocyanatotolylene (51 mg, 0.29 mmol) is added under argon. The solution is stirred for 12 h. Subsequently, 2 ml of degassed isopropanol are added. Finally, the solid is recovered by filtration through a millipore filter and is washed with isopropanol. 238 mg of polymer are obtained, i.e. a yield of 95%.

The physicochemical characterization data are as follows:
[α$_D$]=−96° C. (c=0.345, DMF);
$^1$H NMR (DMSO, 200 MHz): 2.04 ppm (CH$_3$ of the tolyl groups); 4.36 ppm (benzene CH units); 1.25 ppm (isopropyl CH$_3$ groups, the ends of the chains having been deactivated with isopropanol);
$^{31}$P NMR (DMSO, 81 MHz): −15.77 ppm;
Elemental analysis (for 8 monomers)
Calculated: C, 79.06; H, 4.73; N, 5.98; P, 6.22. Found: C, 74.98; H, 5.43; N, 5.90; P, 6.52.

b) Polyurea 2

42 µl (0.29 mmol) of 2,6-diisocyanatotolylene are added to a solution of 200 mg (0.29 mmol) of (S)-6,6'-bis(aminomethyl)-2,2'-bis(diphenylphosphino)-1,1'-binaphthyl in 4 ml of CH$_2$Cl$_2$. The suspension is stirred under argon overnight and then 1 ml of isopropanol is added. After stirring for 2 h, the suspension is filtered and the solid is washed twice with 2 ml of i-PrOH and twice with 2 ml of CH$_2$Cl$_2$. After drying under vacuum, 224 mg of a yellow powder are obtained (93% yield).

[α]$_D$: −96 (c=0.345, DMF);
$^1$H NMR (DMSO): δ=1.21 (d, CH$_3$), 2.04 (s, CH$_3$), 4.36 (s, CH$_2$), 6.64 (d, CH), 6.94 (s, CH), 7.20 (s, CH), 7.32 (s, CH), 7.81 (s, CH), 7.93 (s, CH);
$^{31}$P NMR (DMSO): δ=−15.77;
Elemental analysis:
Calculated: for C$_{745}$H$_{550}$O$_{28}$N$_{50}$P$_{24}$: C, 78.52; H, 4.87; N, 6.15; P, 6.53; O, 3.93. Found: C, 74.98; H, 5.43; N, 5.90; P, 6.52; O, 5.72.

EXAMPLE 2
Preparation of a Ruthenium Catalyst Starting from the Polymer Prepared in Example 1

The catalyst is prepared in situ. All the solvents used were carefully degassed and are anhydrous. The reaction medium is kept under an argon atmosphere. The polymer and the metal precatalyst, bis(2-methylallyl)(cycloocta-1,5-diene) ruthenium, are weighed out directly, in a polymer/metal molar ratio of 1:1, in a 5 ml glass reactor with a conical base removed from the oven and equipped with a stirrer. The reactor is closed by a septum and the air is driven off by an inflow of argon. Acetone is then added, so as to obtain a white suspension comprising 0.006 mol/l of polymer. This suspension is stirred for 30 minutes and then a 0.29M methanolic solution of HBr is added (Ru/Br ratio of 1/2.3). A changing color of the solution, which turns brown, is then observed. This solution is stirred for a further 1 hour and then the solvent is evaporated. The catalyst is then obtained under the appearance of a brown solid.

The catalyst obtained is denoted catalyst of example 2a) when the starting polymer is polyurea 1 and the catalyst obtained is denoted 2b) when the starting polymer is polyurea 2.

EXAMPLE 3

This example illustrates the hydrogenation of α-keto esters in the presence of the ruthenium complex prepared in example 2

The hydrogenation protocol is described below:

Methanol, which has been dried beforehand over magnesium, is added (2.5 ml) under argon to the conical reactor in which the catalyst has just been prepared. The substrate is subsequently added (in a precise catalyst/substrate ratio). The operation consisting in placing under vacuum and in filling the reactor with argon is repeated three times. The septum is then replaced by a pierced stopper and the reactor is placed in an autoclave. The autoclave is purged three times under argon and then three times under hydrogen before receiving 40 bar of hydrogen pressure. The autoclave is placed on a heating plate (50° C.) and stirring is maintained overnight. The conical reactor is finally recovered, the stopper is replaced by a septum and argon is reinjected into this reactor. The reactor is placed in a centrifuge and the solution is extracted using a syringe. The solution is placed in a 50 ml round-bottomed flask and diluted in 20 ml of methanol, ready then to be injected into a chromatography column for gas chromatography for analysis of the activity and enantioselectivity of the reaction.

Hydrogenation was first carried out while selecting methyl pyruvate as substrate. Hydrogenation was then carried out while choosing methyl benzoylformate as substrate.

The enantiomeric excesses are determined by chiral gas chromatography on a column of Macheray-Nagel type (Lipodex A 25 m×0.25 mm for methyl pyruvate and Lipodex E 25×0.25 mm for methyl benzoylformate).

The results obtained are given in the following table 1:

TABLE 1

| Substrate | Catalyst | Degree of conversion (%) | Enantiomeric excess (%) |
|---|---|---|---|
| Methyl pyruvate | example 2a | 82 | 46 |
| Methyl benzoylformate | example 2a | 91 | 26 |

In these examples, the substrate/catalyst molar ratio was set at 1000.

The hydrogenation of methyl benzoylformate results in methyl 2-phenyl-2-hydroxyethanoate and the hydrogenation of methyl pyruvate results in methyl 2-hydroxypropanoate.

EXAMPLE 4

This example illustrates the re-use of the polymer catalyst in the hydrogenation of a β-keto ester.

a) Hydrogenation of a β-keto ester in the presence of freshly prepared catalyst.

The catalyst used is that of example 2a.

The hydrogenation procedure is as described in example 3, except that methyl acetoacetate is used as substrate.

The results obtained appear in table 2 below, it being understood that the method for determining the enantiomeric excesses is that described in example 3.

b) Re-use of the catalyst in the hydrogenation of a β-keto ester

After the hydrogenation reaction carried out in the above stage a), the catalyst is filtered from the reaction medium and recovered.

An identical solution of the β-keto ester in methanol is then added to the solid catalyst. Hydrogenation is then carried out as described above in stage a). This protocol is repeated several times.

The results obtained have been collected in the following table 2.

TABLE 2

| Substrate | Catalyst | Degree of conversion | Enantiomeric excess (%) |
|---|---|---|---|
| Methyl acetoacetate | example 2a | 100 | 95 |
| Methyl acetoacetate | ex. 2a, recovered after a 1st use | 100 | >95 |
| Methyl acetoacetate | ex. 2a, recovered after a 2nd use | 100 | >95 |
| Methyl acetoacetate | ex. 2a, recovered after a 3rd use | 100 | >95 |
| Methyl acetoacetate | ex. 2a, recovered after a 4th use | 100 | >95 |

The hydrogenation of methyl acetoacetate results in methyl 3-hydroxybutanoate.

It is found that the advantageous properties of the catalyst are retained after numerous re-uses. In fact, the enantiomeric excess, which is even improved from the first use after recovery of the catalyst, is maintained above 95% after 4 uses.

EXAMPLE 5

Preparation of a Ruthenium Catalyst Starting from the Polymer Prepared in Example 1

A solution of 5 mg (0.006 mmol) of polymer and 1.3 mg (0.003 mmol) of $[RuCl_2(benzene)]_2$ in 1 ml of dimethylformamide is kept stirred at 100° C. for 30 minutes. After cooling to 50° C., the solvent is evaporated under reduced pressure. After cooling to ambient temperature, the evaporation is continued under reduced pressure (0.1 mbar) to result in the formation of a brown solid.

The catalyst obtained is denoted catalyst of example 5a when the polymer used is that of example 1a and the catalyst obtained is denoted catalyst of example 5b when the starting polymer used is that of example 1b.

EXAMPLE 6

This example illustrates the hydrogenation of β-keto esters.

The hydrogenation protocol is as described in example 3, except that the substrate is selected from methyl 3-oxovalerate, methyl acetoacetate and methyl 3-oxo-6-octenoate, the catalyst used being either the complex prepared in example 2a or the complex prepared in example 5a.

The results obtained have been collected in the following table 3, together with the results reported in the literature in the case of the corresponding hydrogenation reactions using, as catalyst, the equivalent complexes derived from BINAP.

The hydrogenation of methyl acetoacetate results in methyl 3-hydroxybutanoate; the hydrogenation of methyl 3-oxovalerate results in methyl 3-hydroxypentanoate; and the hydrogenation of methyl 3-oxo-6-octenoate results in a mixture of methyl 3-hydroxyoctanoate and methyl 3-hydroxy-6-octenoate.

TABLE 3

| Substrate | Catalyst complex | Substrate/ catalyst molar ratio | Degree of conversion (%) | Enantiomeric excess |
|---|---|---|---|---|
| Methyl acetoacetate | example 2a | 1 000 | 100 | 94 |
| Methyl acetoacetate | BINAP complex, prepared according to the procedure of example 5 | 1 150 | 100 | 99[1] |
| Methyl 3-oxovalerate | example 2a | 1 000 | 100 | 98 |
| Methyl 3-oxovalerate | BINAP complex, prepared according to the procedure of example 5 | 1 200 | 100 | 99[2] |
| Methyl 3-oxo-6-octenoate | example 2a | 1 000 | 90 | 90 |

[1] Kitamura, M., Tokunaga, M., Ohkuma, T. and Noyori, R., Tetrahedron Letters, 32, 1991, 4163–4166
[2] Genet et al., Tetrahedron: Asymmetry, 5, 1994, 675–690.

EXAMPLE 7
Preparation of a Ruthenium Catalyst Starting from the Polymer Prepared in Example 1

A solution of 5 mg (0.006 mmol) of polymer and 1.3 mg (0.003 mmol) of [RuCl$_2$(benzene)]$_2$ in 1 ml of a 1/8 mixture of benzene/ethanol is kept stirred at 50° C. for 2 hours. After cooling to 20° C., the solvent is evaporated under reduced pressure. A brown solid is obtained after evaporating the solvent.

In the same way as above, the catalyst from example 7a is distinguished from the catalyst of example 7b according to whether the starting polymer used is that of example 1a (polyurea 1) or example 1b (polyurea 2).

EXAMPLE 8

This example illustrates the hydrogenation of unsaturated amino acid derivatives.

The hydrogenation protocol is as described in example 3, except that the catalyst, the substrate, the hydrogen pressure and the substrate/catalyst ratio are varied.

The substrate is chosen from a compound of formula:

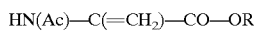

HN(Ac)—C(=CH$_2$)—CO—OR     L1 in which R is H or methyl; and
methyl acetamidocinnamate of formula:

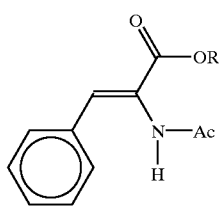

L2 in which R is H or methyl.

Comparative trials were carried out starting from equivalent catalysts derived from BINAP.

The results obtained are summarized in table 4, it being understood that the enantiomeric excess is determined by chiral gas chromatography on a column of Macheray-Nagel type (Lipodex A 25 m×0.25 mm). The hydrogenation of the compounds of formula L1 results in the corresponding compounds of formula HN(Ac)—C(CH$_3$)—CO—OR and the hydrogenation of methyl acetamidocinnamate results in methyl 3-phenyl-2-acetamidopropanoate.

TABLE 4

| Substrate | Catalyst complex | Hydrogenation pressure | Substrate/ catalyst molar ratio | Degree of conversion (%) | Enantiomeric excess (%) |
|---|---|---|---|---|---|
| L1(R = CH$_3$) | example 2b | 40 bar | 100 | 100 | 63 |
| L1(R = CH$_3$) | BINAP complex, prepared according to the procedure of example 2 | 40 bar | 100 | 100 | 67 |
| L1(R = CH$_3$) | example 5b | 40 bar | 100 | 100 | 56 |
| L1(R = CH$_3$) | BINAP complex, prepared according to the procedure of example 5 | 40 bar | 100 | 100 | 78 |
| L1(R = CH$_3$) | example 2a | 40 bar | 1000 | 100 | 94 |
| L1(R = CH$_3$) | BINAP complex, prepared according to the procedure of example 2 | 40 bar | 1000 | 100 | 63 |
| L1(R = CH$_3$) | example 7b | 40 bar | 1000 | 100 | 74 |
| L1(R = H) | example 2b | 40 bar | 200 | 100 | 50 |
| L1(R = H) | example 5a | 10 bar | 100 | 95 | 70 |
| L1(R = H) | example 5b | 40 bar | 100 | 100 | 70 |
| L1(R = H) | BINAP complex, prepared according to the procedure of example 5 | 10 bar | 100 | 95 | 78[1] |
| L1(R = H) | BINAP complex, prepared according to the procedure of example 5 | 40 bar | 200 | 100 | 69 |
| L1(R = H) | BINAP complex, prepared according to the procedure of example 2 | 40 bar | 100 | 100 | 78 |
| L2(R = H) | example 2b | 40 bar | 200 | 100 | 28 |
| L2(R = H) | example 5b | 40 bar | 100 | 100 | 46 |
| L2(R = H) | BINAP complex, prepared according to the procedure of example 5 | 40 bar | 100 | 100 | 74 |

TABLE 4-continued

| Substrate | Catalyst complex | Hydrogenation pressure | Substrate/catalyst molar ratio | Degree of conversion (%) | Enantiomeric excess (%) |
|---|---|---|---|---|---|
| L2(R = CH$_3$) | example 2b | 40 bar | 100 | 100 | 49 |
| L2(R = CH$_3$) | BINAP complex, Prepared according to the procedure of example 2 | 40 bar | 100 | 100 | 72 |
| L2(R = CH$_3$) | example 5b | 40 bar | 100 | 100 | 72 |
| L2(R = CH$_3$) | BINAP complex, prepared according to the procedure of example 5 | 40 bar | 100 | 100 | 80 |
| L2(R = CH$_3$) | example 7a | 40 bar | 100 | 100 | 72 |
| L2(R = CH$_3$) | BINAP complex, prepared according to the procedure of example 7 | 40 bar | 100 | 100 | 74 |

[1]The enantiomeric excess reported in Genet, J.P., Pinel, C., Ratovelomanana-Vidal, V., Mallart, S., Pfister, X;, Cano de Andrade, M. and Laffitte, J.A., Tetrahedron: Asym., 1994, 5, 665, is 75%.

EXAMPLE 9 (Comparative)

In this example, the hydrogenation of an α-keto ester (methyl benzoylformate) and an unsaturated amino acid derivative (methyl 2-acetamidoacrylate) was carried out using, as catalyst, a complex equivalent to the complex of example 2 but comprising 2,2-bis(diphenylphosphino)-1,1'-binaphthyl (BINAP) as such as ligand.

This catalyst is prepared by employing the procedure described in example 2, except that 2,2'-bis(diphenylphospino-1,1'-binaphthyl is used as ligand instead of the polymer.

The procedure for the hydrogenation of methyl benzoylformate and methyl 2-acetamidoacrylate is as described in example 3, except that the catalyst is replaced by the catalyst derived from BINAP.

The results obtained appear in the following comparative table.

COMPARATIVE TABLE

| Substrate | Catalyst | Degree of conversion (%) | Enantiomeric excess (%) |
|---|---|---|---|
| Methyl benzoylformate | BINAP | 98 | 82 |
| Methyl 2-acetamidoacrylate | BINAP | 100 | 64 |

In these examples, the substrate/catalyst molar ratio is set at 1000.

EXAMPLE 10

This example illustrates the hydrogenation of itaconic acid and its dimethyl ester.

The hydrogenation protocol is as illustrated in example 3, except that the hydrogenation pressure, the catalyst complex, the molar ratio of the substrate to the catalyst and the nature of the substrate are varied.

The substrate used has the formula:

$$RO-CO-C(=CH_2)-CH_2-COOR \qquad L3$$

in which R is hydrogen or methyl, and results, after hydrogenation, in the corresponding compound of formula: $RO-CO-C(CH_3)-CH_2-COOR$.

The results obtained on varying the nature of the catalyst are reported in table 5.

TABLE 5

| Substrate | Catalyst complex | Substrate/catalyst molar ration | Hydrogenation pressure | Degree of conversion (%) | Enantiomeric excess (%) |
|---|---|---|---|---|---|
| L3(R = CH$_3$) | example 5b[3] | 100 | 40bar | 100 | 94 |
| L3(R = CH$_3$) | BINAP complex, prepared according to the procedure of example 5[3] | 100 | 40bar | 100 | 94 |
| L3(R = CH$_3$) | example 7a | 100 | 40bar | 100 | 94 |
| L3(R = CH$_3$) | complex derived from the BINAP prepared in example 7 | 100 | 40bar | 100 | >90 (68)[1] |
| L3(R = H) | example 5b[3] | 100 | 40bar | 100 | 71 |
| L3(R = H) | BINAP complex, prepared according to the procedure of example 5[3] | 100 | 40bar | 100 | 88 |
| L3(R = H) | example 7a | 100 | 10bar | 100 | 71 |
| L3(R = H) | complex derived from the BINAP prepared in example 7 | 100 | 10bar | 100 | 82 (98)[2] |

[1]the figure between brackets reports the result obtained in Kawano, H., Ikariya, T., Ishii, Y., Saburi, M., Yoshikawa, S., Uchida, Y. and Kumobayashi, J. Chem. Soc. Perk. Trans., I, 1989, 1571.
[2]the figure between brackets reports the result obtained in Genet, J.P., Pinel, C., Ratovelomanana-Vidal, V., Mallart, S., Pfister, X., Cano de Andrade, M. and Laffitte, J.A., Tetrahedron: Asym., 1994, 5, 685.
[3]the complex used was prepared at 110° C. instead of 100° C.

EXAMPLE 11

This example illustrates the hydrogenation of tiglic acid of formula $CH_3-CH=C(CH_3)-COOH$ under a hydrogen pressure of 40 bar.

The hydrogenation protocol is the same as in example 3, except that the substrate is tiglic acid and that the catalyst is varied.

The reaction conditions and the results obtained are collected in the following table 6, the hydrogenation product being $CH_3-CH_2-CH(CH_3)-COOH$.

TABLE 6

| Catalyst complex | Substrate/ catalyst molar ratio | Degree of conversion (%) | Enantiomeric excess (%) |
|---|---|---|---|
| example 7a complex | 1 000 | 100 | 82 |
| derived from BINAP and prepared as in example 2 | 1 000 | 100 | 80 (90)[(1)] |

[(1)] the figure between brackets reports the result obtained in Genet, J.P., Pinel, C., Ratovelomanana-Vidal, V., Mallart, S., Pfister, X., Cano de Andrade, M. and Laffitte, J.A., Tetrahedron: Asym., 1994, 5, 665.

EXAMPLE 12
Preparation of a Ruthenium Catalyst Starting from the Polymer Prepared in Example 1

In a first step, the preparation is carried out as in example 7. The resulting complex is then dissolved in 1 ml of dimethylformamide, and 2.5 mg (1 eq.) of (S,S)-1,2-diphenylethylenediamine ((S,S)-DPEDA) or (R,R)-1,2-diphenylethylenediamine ((R,R)-DPEDA)) are added. The solution is stirred for 2 hours, the solvent is evaporated under reduced pressure and the complex is used as is.

The catalyst of example 12a is distinguished from the catalyst of example 12b according to whether the starting polymer used is the polymer of example 1a (polyurea 1) or the polymer of example 1b (polyurea 2).

EXAMPLE 13

This example illustrates the hydrogenation of various aromatic ketones.

The hydrogenation protocol is identical to that of example 3, except that a solution of 2.9 mg of potassium tert-butoxide in 0.75 ml (0.0348 mol/l) of isopropanol is used as solvent (instead of methanol) and that 5.8 mmol of substrate are added in each case.

The results obtained are summarized in the following table, it being understood that, in each case, the hydrogenation product is the corresponding alcohol.

TABLE 7

| Substrate | Catalyst complex | Substrate/ catalyst molar ratio | Degree of conversion (%) | Enantiomeric excess (%) |
|---|---|---|---|---|
| phenyl methyl ketone (acetophenone) | example 12a (S,S)-DPEDA | 1 000 | 100 | 68 |
| phenyl methyl ketone (acetophenone) | example 12a (R,R)-DPEDA | 1 000 | 100 | 38 |
| 4'-methoxyacetophenone | example 12a (S,S)-DPEDA | 1 000 | 100 | 62 |
| 4'-(trifluoromethyl)acetophenone | example 12a (S,S)-DPEDA | 1 000 | 100 | 58 |
| 2'-methylacetophenone | example 12a (S,S)-DPEDA | 1 000 | 100 | 92 |

TABLE 7-continued

| Substrate | Catalyst complex | Substrate/ catalyst molar ratio | Degree of conversion (%) | Enantiomeric excess (%) |
|---|---|---|---|---|
| 1-acetylnaphthalene | example 12a (S,S)-DPEDA | 1 000 | 100 | 96 |
| 1-acetylnaphthalene | complex described in (1), derived from BINAP and (S,S)-DPEDA | 500 | 100 | 97[1] |

[1] Doucet, H., Ohkuma, T., Murata, K., Yokozawa, T., Kozawa, M., Kataya, E., England, A. F., Ikariya, T. and Noyori, R., *Angew. Chem. Int. Ed.*, 1998, 37, 1703.

EXAMPLE 14

This example illustrates the re-use of the polymer catalyst in the hydrogenation of an aromatic ketone.

The catalyst used is that of example 12a obtained from (S,S)-diphenylethylenediamine. The procedure used is that of example 13, except that phenyl methyl ketone is used as substrate. The catalyst complex is re-used as illustrated in example 4.

The results are reported in table 8 below, the hydrogenation resulting in each case in 1-phenylethanol.

TABLE 8

| Catalyst complex | Degree of conversion (%) | Enantiomeric excess (%) |
|---|---|---|
| example 12a (S,S)-DPEDA | 100 | 68 |
| example 12a (S,S)-DPEDA recovered after a first use | 100 | 67 |
| example 12a (S,S)-DPEDA recovered after a second use | 100 | 60 |
| example 12a (S,S)-DPEDA recovered after a third use | 100 | 61 |
| example 12a (S,S)-DPEDA recovered after a fourth use | 36 | 61 |

EXAMPLE 15

This example illustrates the hydrogenation of α-keto esters of formula:

R—CO—CO—OCH$_3$ by employing the hydrogenation protocol of example 3 under a hydrogen pressure of 40 bar while varying the nature of the catalyst and the substrate/catalyst ratio.

The product obtained on conclusion of the hydrogenation is R—CH(OH)—COOCH$_3$.

Comparative trials were carried out starting from the equivalent catalysts derived from BINAP.

The results obtained are summarized in table 9, the enantiomeric excess being determined by gas chromatography, as above.

TABLE 9

| Substrate | Catalyst complex | Substrate/ catalyst molar ratio | Degree of conversion (%) | Enantiomeric excess (%) |
|---|---|---|---|---|
| R = CH$_3$ | example 7b | 100 | 100 | 64 |
| R = CH$_3$ | BINAP complex, prepared according to the procedure of example 7 | 100 | 100 | 67 |
| R = C$_6$H$_5$ | example 7b | 100 | 64 | 66 |
| R = C$_6$H$_5$ | BINAP complex, prepared according to the procedure of example 7 | 100 | 93 | 75 |

EXAMPLE 16

This example illustrates the hydrogenation of β-keto esters of formula:

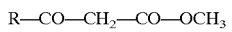

R—CO—CH$_2$—CO—OCH$_3$ by implementing the hydrogenation protocol of example 3 under a hydrogen pressure of 40 bar while varying the nature of the catalyst, the nature of the substrate and the substrate to catalyst molar ratio.

The product obtained on conclusion of the hydrogenation is the corresponding compound of formula R—CH(OH)—CH$_2$—CO—OCH$_3$. Comparative trials were carried out starting from the equivalent catalysts derived from BINAP.

The results obtained are summarized in table 10, the enantiomeric excess being determined by gas chromatography, as above.

TABLE 10

| Substrate | Catalyst complex | Substrate/ catalyst molar ratio | Degree of conversion (%) | Enantiomeric excess (%) |
|---|---|---|---|---|
| R = CH$_3$ | example 5b[(1)] | 1 000 | 100 | 98 |
| R = CH$_3$ | BINAP complex, prepared according to the procedure of example 5[(1)] | 1 000 | 100 | 99 |
| R = CH$_3$ | example 7b | 1 000 | 100 | 99 |
| R = CH$_3$ | BINAP complex, prepared according to the procedure of example 7 | 1 000 | 100 | 99 |
| R = CH$_2$—CH$_3$ | example 2b | 1 000 | 100 | 99 |
| R = CH$_2$—CH$_3$ | BINAP complex, prepared according to the procedure of example 2 | 1 000 | 100 | 99 |

[(1)] the catalyst was prepared at a temperature of 110° C. instead of 100° C.

EXAMPLE 17

This example illustrates the re-use of the polymer catalyst in the hydrogenation of a β-keto ester: methyl acetoacetate.

The catalyst used is that of example 7b. The procedure used is the same as in example 16, the substrate being methyl acetoacetate.

The results obtained are summarized in table 11.

TABLE 11

| Catalyst complex | Degree of conversion (%) | Enantiomeric excess (%) |
|---|---|---|
| example 7b | 100 | 99 |
| example 7b recovered after a first use | 100 | 67 |
| example 7b recovered after a second use | 100 | 60 |
| example 7b recovered after a third use | 100 | 61 |

EXAMPLE 18

Preparation of a Polyamide Starting from (S,S)-6,6'-bis (aminomethyl)-2,2'-bis(diphenylphosphino)-1,1'-binaphthyl (S)-6,6'-Bis(aminomethyl)-2,2'-bis(diphenylphosphino)-1,1'-binaphthyl (100 mg, 0.147 mmol) is dissolved in 4 ml of degassed dimethylacetamide in a 25 ml round-bottomed flask and terephthaloyl chloride (29.8 mg, 0.147 mmol) is added. The mixture is stirred for 24 hours at ambient temperature and then 1 ml of degassed isopropanol is added. After stirring for 1 h, the solvent is evaporated and 70 mg of polymer are obtained, i.e. the yield is 60%.

The physicochemical characterization data are as follows:

$[\alpha]_D$=+66.1 (c=1, DMF)

$^1$H NMR (DMSO, 200 MHz): 1.22 ppm (isopropyl CH$_3$ groups, the ends of the chains having been deactivated with isopropanol), 4.39 ppm (benzyl CH$_2$ groups), 6.7–8.1 ppm (aromatic protons)

$^{31}$P NMR (DMSO, 81 MHz): −15.82 ppm

M.p.>260° C.

EXAMPLE 19

Preparation of a Ruthenium Catalyst Starting from the Polymer Prepared in Example 18

A solution of 10 mg (0.012 mmol) of the polymer of example 18 and 3.1 mg (0.006 mmol) of [RuCl$_2$(benzene)]$_2$ in 1 ml of dimethylformamide is kept stirred at 100° C. for 1 hour. After cooling to 50° C., the solvent is evaporated under reduced pressure. After cooling to ambient temperature, evaporation is continued under reduced pressure (0.1 mbar) to result in the formation of an orange solid.

EXAMPLE 20

This example illustrates the hydrogenation of a β-keto ester, methyl acetoacetate, in the presence of the catalyst of example 19.

Methanol which has been dried beforehand over magnesium is added (3 ml) under argon to the conical reactor in which the catalyst of example 19 has been freshly prepared. The methyl acetoacetate is subsequently added (catalyst/substrate ratio of 1/1000). The operation consisting in applying a vacuum and in filling the reactor with argon is repeated three times. The septum is then replaced by a pierced stopper and then the reactor is placed in an autoclave. The autoclave is purged three times under argon and then three times under hydrogen before receiving 40 bar of hydrogen pressure. The autoclave is placed on a heating plate (50° C.) and stirring is maintained overnight. The reactor is subsequently recovered, the stopper being replaced by a septum, and argon is reinjected into this reactor. The reactor is placed in a centrifuge and then the solution is extracted using a syringe. The solution is placed in a 50 ml round-bottomed flask and diluted in 20 ml of methanol, ready to be injected into a chromatography column for gas chromatography for analysis of the activity and enantioselectivity of the reaction.

The hydrogenation of methyl acetoacetate results in methyl 3-hydroxybutanoate. The enantiomeric excesses are determined by chiral chromatography on a column of Macheray-Nagel type (Lipodex A 25 m×0.25 mm).

The degree of conversion obtained is 100% and the enantiomeric excess is 78%.

EXAMPLE 21

Preparation of a Polyurea Starting from (S,S)-6,6'-bis (aminomethyl)-2,2'-bis(diphenylphosphino)-1,1'-binaphthyl (S)-6,6'-Bis(aminomethyl)-2,2'-bis(diphenylphosphino)-1,1'-binaphthyl (255 mg, 0.375 mmol) is dissolved in 1 ml of degassed dichloromethane in a 25 ml round-bottomed flask under an argon atmosphere and 1,6-diisocyanatohexane (60 ml, 0.375 mmol) is added. The mixture is stirred for 24 hours at ambient temperature and then 1.5 ml of degassed isopropanol are added. After stirring for 1 h, the solid obtained is filtered off and 250 mg of polymer are thus isolated, i.e. a yield of 96%.

$^1$H NMR (d$_6$-DMSO, 200 MHz) (δ: ppm): 1.0–1.3 (m, isopropyl CH$_3$ groups, the ends of the chains having been deactivated with isopropanol), 3.2–3.7 (m, benzyl CH$_2$ groups); 4.2–4.3 (m, CH); 6.5–8.0 (m, aromatic CH units)

$^{31}$P NMR (d$_6$-DMSO, 81 MHz) (δ: ppm): −15.75

MALDI-TOF: 849.5 g; 1526 g; M.p.: >260° C.

EXAMPLE 22

Preparation of a Ruthenium Catalyst Starting from the Polymer Prepared in Example 21

A solution of 0.012 mmol of polymer and 0.006 mmol of [RuCl$_2$(benzene)]$_2$ in 1 ml of dimethylformamide is kept stirred at 100° C. under an argon atmosphere for 1 hour. After cooling to 50° C., the solvent is evaporated under reduced pressure. After cooling to ambient temperature, evaporation is continued under reduced pressure (0.1 mbar) to result in the formation of an orange solid.

What is claimed is:

1. An optically active polymer obtained by polymerization of a chiral diphosphine exhibiting a $C_2$ axis of symmetry, with the exclusion of any other element of symmetry, with one or more polymerizable monomers, said chiral diphosphine being composed of a chiral body carrying two identical functional groups capable of reacting with said polymerizable monomers.

2. The polymer as claimed in claim 1, wherein the functional groups are selected from amino, halogen, hydroxyl, thiol, carboxyl, isocyanate and thioisocyanate functional groups.

3. The polymer as claimed in claim 1, wherein the chiral body of the diphosphine has the structure:

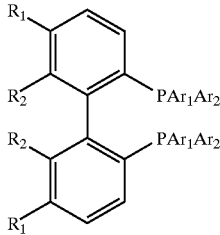

L1 in which:

Ar$_1$ and Ar$_2$ are independently a saturated, unsaturated or aromatic carbocycle;

R$_1$ and R$_2$ are independently a hydrogen atom; a Z group; or an —XZ group where X is O, S or —NT; and Z and T are selected independently from a saturated, unsaturated or aromatic aliphatic hydrocarbonaceous group; or a saturated aliphatic hydrocarbonaceous group substituted by one or more saturated, unsaturated or aromatic carbocyclic groups, in which the aliphatic group is optionally interrupted by O, S and/or N; it being understood that T can additionally be a hydrogen atom; or else two R$_1$ and R$_2$ groups, attached to the same phenyl nucleus, together form an unsaturated or aromatic carbocycle or alternatively together form an unsaturated or aromatic heterocycle.

4. The polymer as claimed in claim 3, wherein:

Ar$_1$ and Ar$_2$ are independently a saturated, unsaturated or aromatic monocyclic carbocycle optionally substituted by one or more ($C_1$–$C_6$) alkyl or ($C_1$–$C_6$)alkoxy groups exhibiting from 3 to 8 carbon atoms;

R$_1$ and R$_2$ are independently selected from the group consisting of a hydrogen atom, a ($C_1$–$C_6$)alkyl group or a ($C_1$–$C_6$)alkoxy group; or else R$_1$ and R$_2$ form, together with the carbon atoms which carry them, (i) an unsaturated or aromatic and monocyclic or polycyclic carbocycle exhibiting from 5 to 13 carbon atoms or (ii) an unsaturated or aromatic and monocyclic or polycyclic heterocycle exhibiting from 4 to 12 carbon atoms and one or more heteroatoms selected from the group consisting of O, S and N, said heterocycle and said carbocycle optionally being substituted by one or more ($C_1$–$C_6$)alkyl or ($C_1$–$C_6$) alkoxy.

5. The polymer as claimed in claim 4, wherein Ar$_1$ and Ar$_2$ are identical and are a phenyl group optionally substituted by one or more ($C_1$–$C_6$) alkyl or ($C_1$–$C_6$) alkoxy; or a ($C_4$–$C_8$) cycloalkyl group optionally substituted by one or more ($C_1$–$C_6$) alkyl groups.

6. The polymer as claimed in claim 3, wherein Ar$_1$ and Ar$_2$ are identical and are cyclohexyl, phenyl or tolyl.

7. The polymer as claimed in claim 3, wherein R$_1$ and R$_2$ are selected independently from a hydrogen atom, ($C_1$–$C_6$) alkyl or ($C_1$–$C_6$) alkoxy or else R$_1$ and R$_2$ form, together with the carbon atoms which carry them, cyclohexenyl with a single unsaturation optionally substituted by one or more ($C_1$–$C_6$)alkyl or ($C_1$–$C_6$) alkoxy; or phenyl optionally substituted by one or more ($C_1$–$C_6$) alkyl or ($C_1$–$C_6$) alkoxy.

8. The polymer as claimed in claim 3, wherein the chiral body of the diphosphine has one of the following structures:

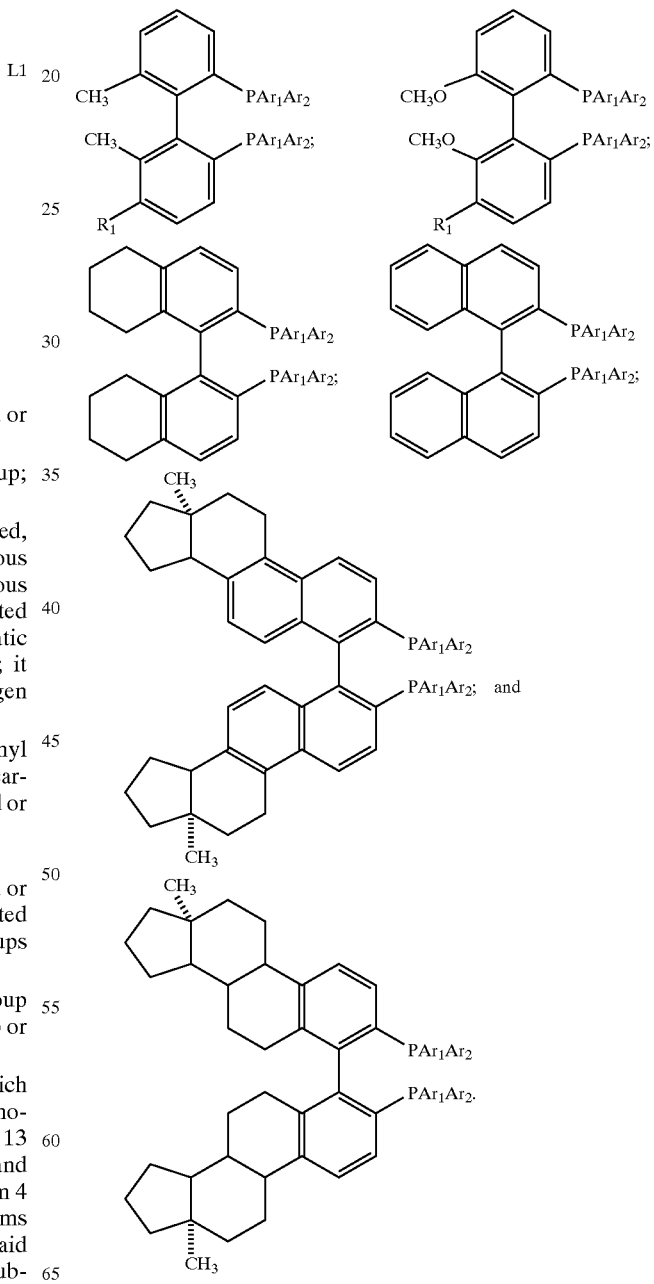

9. The polymer as claimed in claim 1, wherein the chiral body of the diphosphine has the structure:

$$R_5R_6P—A—PR_5R_6 \qquad I.2$$

in which:
- A is a divalent saturated aliphatic hydrocarbonaceous group; a divalent saturated or aromatic carbocyclic group; or a divalent saturated aliphatic hydrocarbonaceous group interrupted by a divalent saturated or aromatic carbocyclic group;
- $R_5$ and $R_6$ are different and are a saturated aliphatic hydrocarbonaceous group; or an aromatic carbocyclic or aromatic heterocyclic group.

10. The polymer as claimed in claim 9, wherein:
A is a $C_1$–$C_6$ alkylene chain optionally substituted by one or more $(C_1$–$C_6)$ alkoxy, $di(C_1$–$C_6)$ alkylamino or $(C_1$–$C_6)$alkylthio groups; a $(C_3$–$C_8)$cycloalkylene group optionally substituted by one or more $(C_1$–$C_6)$ alkoxy, $di(C_1$–$C_6)$ alkylamino or $(C_1$–$C_6)$ alkylthio groups; a $(C_6$–$C_{10})$ arylene group optionally substituted by one or more $(C_1$–$C_6)$ alkoxy, $di(C_1$–$C_6)$ alkylamino or $(C_1$–$C_6)$alkylthio groups; or a —$(CH_2)_j$—B"—$(CH_2)_j$— group where j is an integer from 1 to 3 and B" is $(C_3$–$C_8)$ cycloalkylene optionally substituted by one or more $(C_1$–$C_6)$ alkoxy, $di(C_1$–$C_6)$ alkylamino or $(C_1$–$C_6)$ alkylthio or $(C_6$–$C_{10})$ arylene optionally substituted by one or more $(C_1$–$C_6)$ alkoxy, $di(C_1$–$C_6)$ alkylamino or $(C_1$–$C_6)$ alkylthio;
$R_5$ and $R_6$ are different and are an aromatic monocyclic heterocycle exhibiting from 3 to 7 carbon atoms and one or more heteroatoms chosen from O, N and S; a $(C_6$–$C_{10})$ aryl group, said heterocycle and said aryl group optionally being substituted by one or more $(C_1$–$C_6)$ alkyl or $(C_1$–$C_6)$ alkoxy groups; or else $(C_1$–$C_6)$ alkyl optionally substituted by one or more $(C_1$–$C_6)$alkoxy.

11. The polymer as claimed in claim 10, wherein A is ethylene.

12. The polymer as claimed in claim 10, wherein $R_5$ and $R_6$ are independently selected from phenyl optionally substituted by one or more $(C_1$–$C_6)$ alkyl or $(C_1$–$C_6)$ alkoxy.

13. The polymer as claimed in claim 10, wherein the chiral body of the diphosphine has the structure:

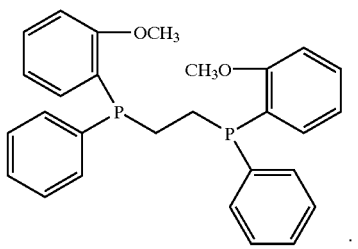

14. The polymer as claimed in claim 1, wherein the chiral body of the diphosphine has the structure:

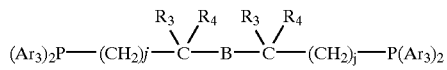

in which:
- * denotes an asymmetric center;
- i is 0 or 1;

$R_3$ and $R_4$ are independently a hydrogen atom or a saturated aliphatic hydrocarbonaceous group or else the $R_4$ radicals are as defined above and the $R_3$ radicals together form a divalent saturated aliphatic hydrocarbonaceous chain optionally interrupted by two X groups, X being as defined above in claim 3;
B is a bond or else is as defined above for A in claim 9;
$Ar_3$ is as defined above for $R_5$ and $R_6$ in claim 9.

15. The polymer as claimed in claim 14, wherein:
$R_3$ and $R_4$ are selected independently from a hydrogen atom and a $(C_1$–$C_6)$alkyl group; or else the two $R_3$ groups together form a $(C_1$–$C_6)$ alkylene chain optionally interrupted by two oxygen or sulfur atoms, and $R_4$ is as defined above;
B is a bond or else is as defined above for A in claim 7;
$Ar_3$ is an aromatic monocyclic heterocycle exhibiting from 3 to 7 carbon atoms and one or more heteroatoms selected from the group consisting of O, N and S; a $(C_6$–$C_{10})$ aryl group, said heterocycle and said aryl group optionally being substituted by one or more $(C_1$–$C_6)$ alkyl or $(C_1$–$C_6)$ alkoxy groups; or else $(C_1$–$C_6)$ alkyl optionally substituted by one or more $(C_1$–$C_6)$ alkoxy.

16. The polymer as claimed in claim 15, wherein $Ar_3$ is phenyl optionally substituted by one or more $(C_1$–$C_6)$alkyl or $(C_1$–$C_6)$alkoxy.

17. The polymer as claimed in claim 15, wherein the chiral body of the diphosphine has one of the following structures:

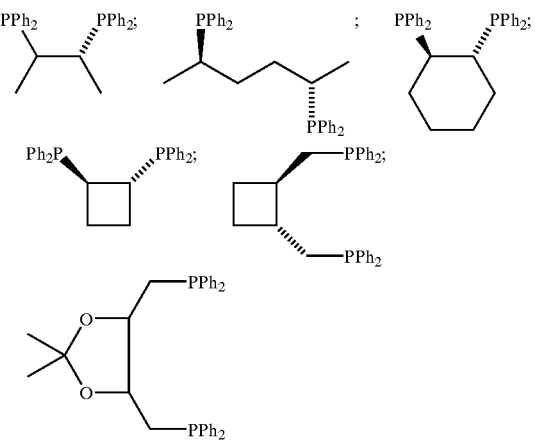

where Ph is phenyl, or one of the enantiomeric forms of these structures.

18. The polymer as claimed in claim 1, wherein the chiral body of the diphosphine has the structure:

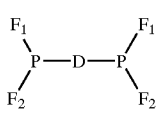

in which:
- D is as defined above for A in claim 9;
- $F_1$ and $F_2$ are identical and are a saturated aliphatic hydrocarbonaceous group, said group carrying at least one chiral center; a saturated carbocyclic group carrying at least one chiral center; or alternatively
- $F_1$ and $F_2$ together form a divalent saturated aliphatic hydrocarbonaceous chain optionally interrupted by two X groups, wherein X is O, S or —NT, two of the carbons of said chain constituting asymmetric centers.

19. The polymer as claimed in claim 18, wherein:

D is a $C_1$–$C_6$ alkylene chain optionally substituted by one or more ($C_1$–$C_6$) alkoxy, di($C_1$–$C_6$) alkylamino or ($C_1$–$C_6$)alkylthio groups; a ($C_3$–$C_8$)cycloalkylene group optionally substituted by one or more ($C_1$–$C_6$) alkoxy, di($C_1$–$C_6$) alkylamino or ($C_1$–$C_6$) alkylthio groups; a ($C_6$–$C_{10}$)arylene group optionally substituted by one or more ($C_1$–$C_6$) alkoxy, di($C_1$–$C_6$) alkylamino or ($C_1$–$C_6$)alkylthio groups; or a —$(CH_2)_j$—B"—$(CH_2)_j$— group where j is an integer between 1 and 3 and B" is ($C_3$–$C_8$)cycloalkylene (optionally substituted by one or more ($C_1$–$C_6$) alkoxy, di($C_1$–$C_6$) alkylamino or ($C_1$–$C_6$) alkylthio)or ($C_6$–$C_{10}$) arylene (optionally substituted by one or more ($C_1$–$C_6$) alkoxy, di($C_1$–$C_6$) alkylamino or ($C_1$–$C_6$) alkylthio groups);

$F_1$ and $F_2$ are identical and are ($C_1$–$C_6$) alkyl optionally substituted by one or more ($C_1$–$C_6$) alkoxy, said alkyl group carrying at least one chiral center; ($C_3$–$C_8$) cycloalkyl substituted by one or more ($C_1$–$C_6$) alkoxy or ($C_1$–$C_6$) alkyl, said cycloalkyl carrying at least one chiral center; or else $F_1$ and $F_2$ together form a ($C_1$–$C_6$) alkylene chain optionally interrupted by two oxygen or sulfur atoms, said chain being substituted by one or more ($C_1$–$C_6$) alkyl or ($C_1$–$C_6$) alkoxy groups, two of the carbons of said chain constituting asymmetric centers.

20. The polymer as claimed in claim 18, wherein the chiral body of the diphosphine has the structure:

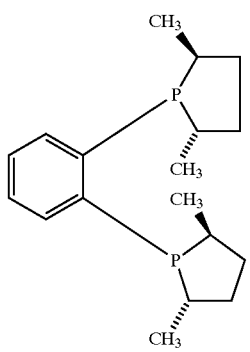

or some diastereoisomeric form.

21. The polymer as claimed in claim 1, wherein said diphosphine is composed of a chiral body carrying two —$CH_2NH_2$ groups.

22. The polymer as claimed in claim 21, having, for a repeat unit:

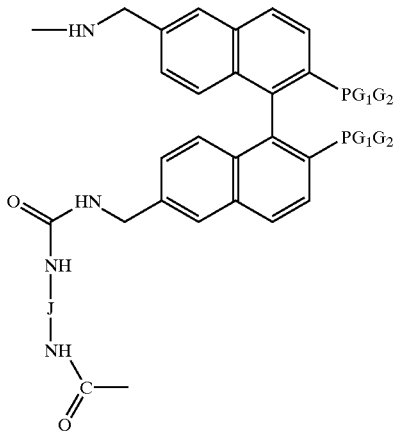

in which $G_1$ and $G_2$ are independently a saturated or aromatic carbocyclic group; and J is a divalent hydrocarbonaceous radical with an aliphatic, alicyclic and/or aromatic nature;

the degree of polymerization being between 2 and 100.

23. The polymer as claimed in claim 1, wherein the polymer can be obtained by polymerization of said diphosphine with a polymerizable monomer exhibiting a $C_2$ axis of symmetry or plane of symmetry.

24. The polymer as claimed in claim 1, wherein the polymerizable monomers are diisocyanates.

25. The process for the preparation of the optically active polymer as claimed in claim 1, wherein a chiral diphosphine exhibiting a $C_2$ plane of symmetry, with the exclusion of any other element of symmetry, is polymerized with one or more polymerizable monomers, said chiral diphosphine comprising a chiral body carrying two identical functional groups capable of reacting with said polymerizable monomers.

26. A ligand for the preparation of a metal complex for use in asymmetric catalysis comprising the polymer as claimed in claim 1.

27. The ligand as claimed in claim 26, wherein the metal complex is a ruthenium or rhodium complex.

28. A method for conducting the hydrogenation of C=O bonds or C=C bonds comprising using the ligand as claimed in claim 27.

29. A racemic polymer, corresponding to the polymer as claimed in claim 1.

30. A method for the selective reduction of ketones comprising using a combination of the optionally active polymers as claimed in claim 1 with a diamine.

31. A method for the selective reduction of ketones comprising using a combination of the racemic polymer as claimed in claim 29 with a chiral diamine.

32. The method as claimed in claim 30, in which the diamine is 1,2-diamino-1,2-diphenylethane.

33. The polymer as claimed in claim 21, having, for repeat unit:

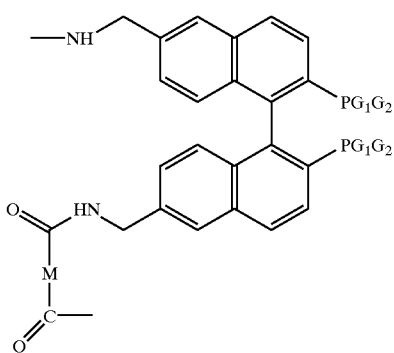

in which
- G₁ and G₂ are independently a saturated or aromatic carbocyclic group; and
- J is a divalent hydrocarbonaceous radical with an aliphatic, alicyclic and/or aromatic nature.

34. An optically active polymer comprising: a residue of a chiral diphosphine exhibiting a $C_2$ axis of symmetry, with the exclusion of any other element of symmetry, and comprising two identical polymerizable functional groups; and a residue of a monomer which can polymerize with the two functional groups, wherein the optically active polymer has more than one chiral site per polymeric chain and wherein the polymer is obtained by polymerization of the chiral diphosphine, with one or more of the polymerizable monomers, the chiral diphosphine being composed of a chiral body carrying the two identical functional groups capable of reacting with the polymerizable monomers.

35. An optically active polymer comprising: a residue of a chiral diphosphine exhibiting a $C_2$ axis of symmetry, with the exclusion of any other element of symmetry, and comprising two identical polymerizable functional groups; and a residue of a monomer which can polymerize with the two functional groups, wherein the optically active polymer has more than one chiral site per polymeric chain and wherein the polymer is obtained by polymerization of the chiral diphosphine, with one or more of the polymerizable monomers, the chiral diphosphine being composed of a chiral body carrying the two identical functional groups capable of reacting with the polymerizable monomers, and wherein the functional groups are selected from the group consisting of an amino, a halogen, a hydroxyl, a thiol, a carboxyl, an isocyanate and a thioisocyanate functional group.

36. A method of making an optically active polymer, the method comprising polymerizing a chiral diphosphine exhibiting a $C_2$ axis of symmetry, with the exclusion of any other element of symmetry, with one or more polymerizable monomers, said chiral diphosphine being composed of a chiral body carrying two identical functional groups capable of reacting with said polymerizable monomers.

\* \* \* \* \*